(12) United States Patent
Arthur et al.

(10) Patent No.: US 12,062,441 B2
(45) Date of Patent: Aug. 13, 2024

(54) PERSONAL PROTECTIVE EQUIPMENT AND SAFETY MANAGEMENT SYSTEM HAVING ACTIVE WORKER SENSING AND ASSESSMENT

(71) Applicant: 3M INNOVATIVE PROPERTIES COMPANY, St. Paul, MN (US)

(72) Inventors: Jonathan B. Arthur, Hudson, WI (US); Craig M. Carlson, Vadnais Heights, MN (US); Joel S. Graf, Vadnais Heights, MN (US); Karim Z. Mansour, St. Paul, MN (US); Karl W. Bloedorn, Oakdale, MN (US); Lyle L. Luppes, Rosemount, MN (US); Caroline M. Ylitalo, Stillwater, MN (US); Katherine L. Sheely, Stillwater, MN (US); Kevin D. Landgrebe, Woodbury, MN (US); Katri M. Huikko, Cottage Grove, MN (US); Chin-Yee Ng, Oakdale, MN (US); Ranjani V. Parthasarathy, Woodbury, MN (US); Federica Sgolastra, Woodbury, MN (US); Katie F. Wlaschin, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 694 days.

(21) Appl. No.: 17/250,118

(22) PCT Filed: May 31, 2019

(86) PCT No.: PCT/IB2019/054533
§ 371 (c)(1),
(2) Date: Dec. 1, 2020

(87) PCT Pub. No.: WO2019/234569
PCT Pub. Date: Dec. 12, 2019

(65) Prior Publication Data
US 2021/0233654 A1  Jul. 29, 2021

Related U.S. Application Data

(60) Provisional application No. 62/680,214, filed on Jun. 4, 2018.

(51) Int. Cl.
*G16H 40/63* (2018.01)
*G16H 50/30* (2018.01)

(52) U.S. Cl.
CPC .............. *G16H 40/63* (2018.01); *G16H 50/30* (2018.01)

(58) Field of Classification Search
CPC .. G06Q 50/20–26; G16H 50/30; G16H 40/63; G16H 40/67
(Continued)

(56) References Cited

U.S. PATENT DOCUMENTS

| 8,830,068 B2 | 9/2014 | Campbell |
| 9,220,444 B2 | 12/2015 | Russell |

(Continued)

FOREIGN PATENT DOCUMENTS

| WO | WO 2014-070801 | 5/2014 | |
| WO | WO-2016089708 A1 * | 6/2016 | ............. G06F 19/00 |

(Continued)

OTHER PUBLICATIONS

Horseman, S. et al. "Adding the Predictive P into Personal Protective Equipment." Paper presented at the SPE International Conference and Exhibition on Health, Safety, Security, Environment, and Social Responsibility, Abu Dhabi, UAE, Apr. 2018. Abstract. doi: https://doi.org/10.2118/190579-MS (Year: 2018).*

(Continued)

*Primary Examiner* — Christopher L Gilligan
*Assistant Examiner* — Jessica Marie Webb
(74) *Attorney, Agent, or Firm* — Sriram Srinivasan

(57) ABSTRACT

A system includes a computing device a personal protective equipment (PPE) device. The PPE device is configured to be worn by a worker and includes and at least one physiological
(Continued)

sensor configured to generate physiological data indicative of one or more physiological characteristics of a worker. The computing device is configured to determine a safety risk score for the worker based at least in part on the physiological data and a risk profile associated with the worker.

16 Claims, 6 Drawing Sheets

(58) Field of Classification Search
USPC .................................................. 705/2, 3, 4
See application file for complete search history.

(56) References Cited

U.S. PATENT DOCUMENTS

| | | | |
|---|---|---|---|
| 9,232,040 B2 | 1/2016 | Barash | |
| 9,433,372 B2 | 9/2016 | Russell | |
| 2003/0144829 A1 | 7/2003 | Geatz | |
| 2004/0078219 A1 | 4/2004 | Kaylor | |
| 2012/0165616 A1* | 6/2012 | Geva | A61B 5/0022 |
| | | | 600/300 |
| 2013/0065257 A1 | 3/2013 | Wang | |
| 2013/0116578 A1 | 5/2013 | An | |
| 2013/0144131 A1 | 6/2013 | Wang | |
| 2013/0218022 A1 | 8/2013 | Larsen | |
| 2014/0005497 A1 | 1/2014 | Larsen | |
| 2014/0322617 A1 | 10/2014 | Wang | |
| 2015/0123787 A1 | 5/2015 | Watson | |
| 2015/0126834 A1 | 5/2015 | Wang | |
| 2015/0164374 A1 | 6/2015 | Russell | |
| 2015/0186602 A1 | 7/2015 | Pipke | |
| 2015/0213225 A1* | 7/2015 | Amarasingham | G16H 50/30 |
| | | | 705/2 |
| 2016/0354039 A1* | 12/2016 | Soto | A61B 5/74 |
| 2017/0061093 A1* | 3/2017 | Amarasingham | G16H 10/60 |
| 2017/0132884 A1 | 5/2017 | Kumar | |
| 2017/0199979 A1* | 7/2017 | Reiner | G16H 10/60 |
| 2017/0330446 A1* | 11/2017 | Thurlow | H04W 4/029 |
| 2018/0033279 A1* | 2/2018 | Chong | G06Q 10/0633 |
| 2018/0204155 A1* | 7/2018 | Bradbury | G06Q 10/0637 |

FOREIGN PATENT DOCUMENTS

| | | | |
|---|---|---|---|
| WO | WO 2017-223438 | 12/2017 | |
| WO | WO-2017223438 A1 * | 12/2017 | ............. A41D 13/12 |
| WO | WO-2018071568 A1 * | 4/2018 | ............... A42B 3/30 |

OTHER PUBLICATIONS

E. Gaura, J. Kemp and J. Brusey, "Leveraging Knowledge From Physiological Data: On-Body Heat Stress Risk Prediction With Sensor Networks," in IEEE Transactions on Biomedical Circuits and Systems, vol. 7, No. 6, pp. 861-870, Dec. 2013, doi: 10.1109/TBCAS.2013.2254485. (Year: 2013).*

Kastellorizios, "Continuous Metabolic Monitoring Based on Multi-Analyte Biomarkers to Predict Exhaustion", Nature: Scientific Reports, 2015, pp. 1-8.

Rathee, "Biosensors Based on Electrochemical Lactate Detection: A Comprehensive Review", Biochemistry and Biophysics Reports, 2016, vol. 05, pp. 35-54.

Sakharov, "Relationship Between Lactate Concentrations in Active Muscle Sweat and Whole Blood", Bulletin of Experimental Biology and Medicine, 2010, vol. 150, No. 01, pp. 83-85.

Sandulescu, "Wearable System for Stress Monitoring of Firefighters in Special Missions", E-Health and Bioengineering Conference (EHB), IEEE, 2015, pp. 1-4, XP03285498.

International Search Report for PCT International Application No. PCT/IB2019/054533, mailed on Sep. 10, 2019, 5 pages.

* cited by examiner

PERSONAL PROTECTIVE EQUIPMENT AND SAFETY MANAGEMENT SYSTEM HAVING ACTIVE WORKER SENSING AND ASSESSMENT

CROSS REFERENCE TO RELATED APPLICATIONS

This application is a national stage filing under 35 U.S.C. 371 of PCT/IB2019/054533, filed May 31, 2019, which claims the benefit of U.S. Provisional Application No. 62/680,214, filed Jun. 4, 2018, the disclosure of which is incorporated by reference in its/their entirety herein.

TECHNICAL FIELD

The present disclosure relates to worker safety and computing systems related to improving worker safety.

BACKGROUND

Many work environments include hazards that may expose people working within a given environment to a safety event, such as a fall, breathing contaminated air, or temperature related injuries (e.g., heat stroke, frostbite, etc.). Workers may utilize personal protective equipment (PPE) to help mitigate the risk of a safety event. A worker may not recognize an impending safety event until the environment becomes too dangerous or the worker's health deteriorates too far.

SUMMARY

In general, the present disclosure describes techniques for detecting and dynamically responding to safety risks to workers operating in or being considered for operating in work environments. A worker in a work environment may be exposed to various hazards or safety events (e.g., air contamination, heat, falls, etc.). A worker may utilize personal protective equipment (PPE) that includes one or more physiological sensors that monitor corresponding physiological conditions of the worker in the environment and provide physiological data indicating the physiological conditions to a worker safety management system. In addition, one or more environmental sensors, such as thermometers or gas detectors, located in the work environment may monitor corresponding environmental conditions of the environment and provide environmental data indicating the environmental conditions to the worker safety management system. The worker safety management system may provide a customized risk assessment for a worker in the environment by determining a safety risk score for the worker that is based on the dynamic physiological data and on a risk profile associated with the worker or a class of workers that includes the worker. In some cases, the worker safety management system may determine the safety risk score for the worker further based on the environmental data.

In some examples, the risk profile includes a personal risk profile for the worker. For example, the personal risk profile for the worker may include historical physiological data for the worker. In some examples, the worker safety management system may provide a risk assessment for the worker based at least in part on physiological data for one or more additional workers. For example, the worker safety management system may determine the risk to a given worker based on physiological data for the worker and historical or current physiological data for one or more additional workers. In other words, a system may include one or more physiological sensors that concurrently monitor the physiological conditions of the workers and the one or more additional workers. In such examples, the safety risk score may indicate a risk to the worker relative to the one or more additional workers and within a specific environment. In some examples, the system identifies the one or more additional workers by identifying workers that are similar to the worker. The system may identify similar workers based on biographical information, the work environment, tasks to be performed, etc.

The worker safety management system may output an indication of the safety risk score computed for a given worker. For example, the worker safety management system may output an indication of the score for display by a display device. As another example, the system may output an alert based on the safety risk score. For example, the worker safety management system may determine whether the safety risk score satisfies (e.g., is greater than) a threshold score and may output an alert (e.g., visual, audible, tactile, etc.) indicating the safety risk score satisfies the threshold. In some examples, the system may output alert to a computing device worn or operable by the worker to alert the worker he or she is at higher risk. As another example, the system output the alert to a computing operable by a safety supervisor, which may enable the safety supervisor to assist the worker or replace the worker with another worker, which may increase worker safety.

The techniques described herein may provide one or more technical advantages to systems for worker safety and safety management. For example, the techniques may enable a worker safety management system to improve worker safety by incorporating, into a risk assessment, physiological data for workers operating in or being considered for operating in a hazardous environment and calibrating risks to workers based on their risk profiles. As another example, the techniques may enable a worker safety management system to make risk assessments in part by calibrating workers' risks in view of data from multiple physiological sensors generating physiological data for multiple workers. This peer comparison and inter-worker sensor calibration may highlight a worker experiencing outlier physiological conditions among multiple workers in a given work environment and may decrease the collective risk to the pool of workers by increasing the likelihood of selecting the worker least likely to experience a safety event remaining in a given work environment.

In one example, the disclosure describes a system that includes a computing device and a personal protective equipment (PPE) device. The PPE device is configured to be worn by a worker and includes at least one physiological sensor configured to generate physiological data indicative of one or more physiological characteristics of a worker. The computing device is configured to determine, based at least in part on the physiological data and a risk profile associated with the worker, a safety risk score for the worker; and output an indication of the safety risk score for the worker.

In another example, the disclosure describes a computing device that includes memory and at least one processor. The memory includes instructions that, when executed, cause the at least one processor to: receive, from at least one physiological sensor, physiological data indicative of one or more physiological characteristics of a worker; determine, based at least in part on the physiological data and a risk profile associated with the worker, a safety risk score for the worker; and output an indication of the safety risk score for the worker.

In another example, the disclosure describes means for generating physiological data indicative of one or more physiological characteristics of a worker; means for determining, based at least in part on the physiological data and a risk profile associated with the worker, a safety risk score for the worker; and means for outputting an indication of the safety risk score for the worker.

The details of one or more examples of the disclosure are set forth in the accompanying drawings and the description below. Other features, objects, and advantages of the disclosure will be apparent from the description and drawings, and from the claims.

It is to be understood that the embodiments may be utilized and structural changes may be made without departing from the scope of the invention. The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
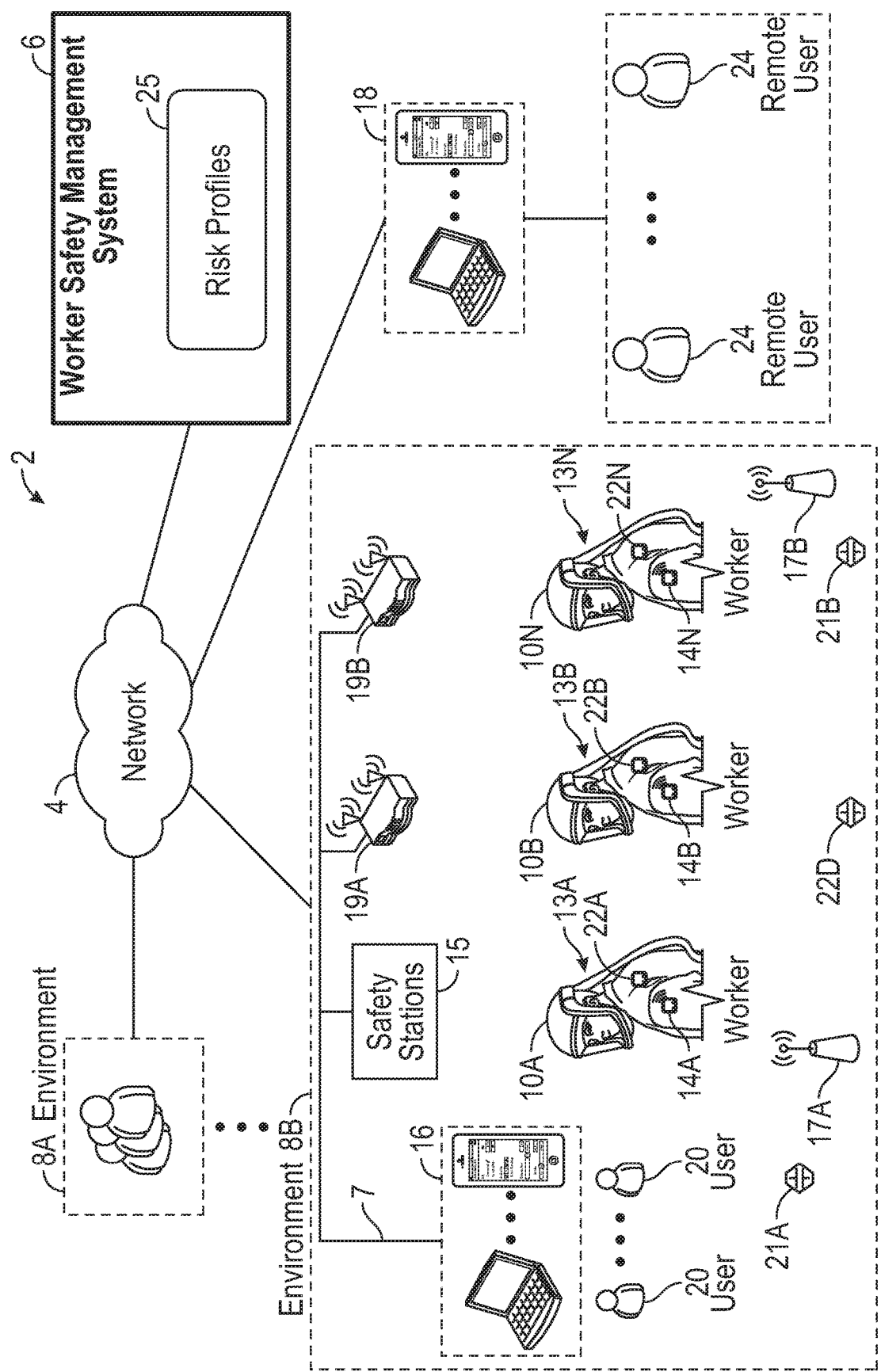
FIG. 1 is a block diagram illustrating an example system that includes a worker safety management system, in accordance with various techniques of this disclosure.

FIG. 1 is a block diagram illustrating an example system 2 that includes a worker safety management system (SMS) 6 for dynamically managing risks to workers, according to techniques described in this disclosure. In general, SMS 6 may provide data acquisition, monitoring, activity logging, reporting, predictive analytics, safety condition identification, and alert generation. For example, SMS 6 includes an underlying analytics and safety management engine and alerting system in accordance with various examples described herein. In general, SMS 6 may manage risk to workers by determining a personalized safety risk score for a worker based on the physiological conditions of the worker and a personalized risk profile associated with the worker. For example, SMS 6 may receive physiological data indicative of physiological conditions of the worker from a physiological sensor. Physiological sensors may include breathing monitors, heart rate monitors, sweat monitors, to name only a few examples. The personalized risk profile may include historical physiological data for the worker, physiological data (e.g., current and/or historical) for other workers, biographical information for the workers and/or other workers, etc. By analyzing physiological conditions of the worker and a personalized risk profile associated with the worker, SMS 6 may manage risk to workers in a variety of work environments.

As further described below, SMS 6 may provide an integrated, end-to-end system for managing risk to workers 10 within one or more physical environments 8, which may be construction sites, mining or manufacturing sites or any physical environment. The techniques of this disclosure may be realized within various parts of computing environment 2.

As shown in the example of FIG. 1, system 2 represents a computing environment in which computing device(s) within a plurality of physical environments 8A, 8B (collectively, environments 8) electronically communicate with SMS 6 via one or more computer networks 4. Each of physical environment 8 represents a physical environment, such as a work environment, in which one or more individuals, such as workers 10, utilize personal protective equipment 13 while engaging in tasks or activities within the respective environment.

In this example, environment 8A is shown as generally as having workers 10, while environment 8B is shown in expanded form to provide a more detailed example. In some examples, one or more physiological sensors 22A-22D (collectively, physiological sensors 22) are configured to detect one or more physiological characteristics of one or more workers 10. Examples of physiological sensors 22 include a heart rate sensor (e.g., configured to detect a pulse or determine a heart rate of worker 10A), breathing sensor (e.g., configured to detect a breathing rate), temperature sensor (e.g., configured to detect a temperature of worker 10A), sweat sensor (e.g., configured to detect how much worker 10A is sweating), among other examples. Physiological sensors 22 generate and output physiological data indicative of the one or more physiological characteristics detected from the one or more workers 10. For example, when physiological sensor 22A includes a heart rate sensor, the heart rate sensor may output data indicative of a heart rate of worker 10A. As another example, when physiological sensor 22A includes a temperature sensor, the temperature sensor may output data indicative of a temperature (e.g., core body temperature or skin temperature) of the worker 10A. In some examples, physiological sensor 22A may include a biosensor configured to measure biomarkers in body fluids (e.g., saliva, breath, tears and/or interstitial fluids), and may output data indicative of the biomarkers. For example, physiological sensor 22A may include a cutaneous or subcutaneous analyte sensor (e.g., a sweat sensor) configured to measure biomarkers in sweat of a worker and to output data indicative of perspiration of worker 10A.

In some examples, physiological sensors 22 may be included as part of personal protective equipment. For example, as illustrated in FIG. 1, PPE 13A-13N each include one or more physiological sensors 22A-22C. In some examples, one or more of physiological sensors 22 may be separate from any articles of personal protective equipment. For example, as illustrated in FIG. 1, physiological sensor 22D is physically distinct from any articles of personal protective equipment. Physiological sensor 22D may be worn by worker 10A (e.g., PPE PPE 13A may include a so-called smartwatch or fitness tracker) or may be a remote sensor physically separate from worker 10A (e.g., an infrared camera that monitors the body temp of one or more workers 10).

As shown in the example of FIG. 1, an environment, such as environment 8B, may also contain one or more wireless-enabled beacons, such as beacons 17A-17B, that provide accurate location data within the work environment. For example, beacons 17A-17B may be GPS-enabled such that a controller within the respective beacon may be able to precisely determine the position of the respective beacon. Based on wireless communications with one or more of beacons 17, a given PPE 13 or communication hub 14 worn by a worker 10 is configured to determine the location of the worker within environment 8B. In this way, event data reported to SMS 6 may be stamped with positional data to aid analysis, reporting and analytics performed by SMS 6.

In addition, an environment, such as environment 8B, may also include one or more wireless-enabled sensing stations, such as sensing stations 21A, 21B. Each sensing station 21 includes one or more sensors and a controller configured to output data indicative of sensed environmental conditions. Moreover, sensing stations 21 may be positioned within respective geographic regions of environment 8B or otherwise interact with beacons 17 to determine respective positions and include such positional data when reporting environmental data to SMS 6. As such, SMS 6 may be configured to correlate the sensed environmental conditions with the particular regions and, therefore, may utilize the captured environmental data when processing event data received from PPE 13, sensing stations 21, or physiological sensors 22. For example, SMS 6 may utilize the environmental data to aid generating alerts or other instructions for PPE 13 and for performing predictive analytics, such as determining any correlations between certain environmental conditions (e.g., heat, humidity, visibility) with abnormal worker behavior or increased safety events. As such, SMS 6 may utilize current environmental conditions to aid prediction and avoidance of imminent safety events. Example environmental conditions that may be sensed by sensing stations 21 include but are not limited to temperature, humidity, presence of gas, pressure, visibility, wind and the like. Safety events may refer to heat related illness or injury, cardiac related illness or injury, respiratory related illness or injury, or eye or hearing related injury or illness.

In the example of FIG. 1, a plurality of workers 10A-10N are shown as utilizing PPE 13A-13N. However, in some examples, the techniques of this disclosure apply to workers that are not utilizing PPE. Although PPE 13 in the example of FIG. 1 are illustrated as respirators, the techniques described herein apply to other types of PPE, such as those for hearing protection, vision protection, and head protection, as well as protective clothing, trauma protection, other PPE for assisted/protective respiration, and so forth. In some examples, PPE 13 include computerized devices, such as a watch (e.g., a smartwatch), fitness tracker, eyewear, headphones, mobile phone, heart rate monitor, pulse oximeter, or other wearable device that may include one or more physiological sensors 22.

Each of PPE 13 may in some examples include embedded sensors or monitoring devices and processing electronics configured to capture data (also referred to as data) in real-time as a user (e.g., worker) engages in activities while utilizing (e.g., wearing) the PPE. PPE 13 may include a number of equipment sensors for sensing or controlling the operation of such components. A head top may include, as examples, a head top visor position sensor, a head top temperature sensor, a head top motion sensor, a head top impact detection sensor, a head top position sensor, a head top battery level sensor, a head-top head detection sensor, an ambient noise sensor, or the like. A blower may include, as examples, a blower state sensor, a blower pressure sensor, a blower run time sensor, a blower temperature sensor, a blower battery sensor, a blower motion sensor, a blower impact detection sensor, a blower position sensor, or the like. A filter may include, as examples, a filter presence sensor, a filter type sensor, or the like. Each of the above-noted equipment sensors may generate usage data, as described herein. In some examples, one or more articles of PPE worn by workers 10 include one or more physiological sensors 22. In some examples, one or more articles of PPE worn by workers 10 include one or more sensing stations 21.

In addition, each of PPE 13 may include one or more output devices for outputting data that is indicative of operation of PPE 13 and/or generating and outputting communications to the respective worker 10. For example, PPE 13 may include one or more devices to generate audible feedback (e.g., one or more speakers), visual feedback (e.g., one or more displays, light emitting diodes (LEDs) or the like), or tactile feedback (e.g., a device that vibrates or provides other haptic feedback).

In general, each of environments 8 include computing facilities (e.g., a local area network) by which physiological sensors 22, sensing stations 21, beacons 17, and/or PPE 13 are able to communicate with SMS 6. For examples, environments 8 may be configured with wireless technology, such as 802.11 wireless networks, 802.15 ZigBee networks, and the like. In the example of FIG. 1, environment 8B includes a local network 7 that provides a packet-based transport medium for communicating with SMS 6 via network 4. Environment 8B may include wireless access point 19 to provide support for wireless communications. In some examples, environment 8B may include a plurality of wireless access points 19 that may be geographically distributed throughout the environment to provide support for wireless communications throughout the work environment.

In some examples, each worker 10 may be equipped with a respective one of wearable communication hubs 14A-14N that enable and facilitate wireless communication between SMS 6 and physiological sensors 22, sensing stations 21, beacons 17, and/or PPE 13. For example, physiological sensors 22, sensing stations 21, beacons 17, and/or PPE 13 may communicate with a respective communication hub 14 via wireless communication (e.g., Bluetooth or other short-range protocol), and the communication hubs may communicate with SMS 6 via wireless communications processed by wireless access point 19. Although shown as wearable devices, hubs 14 may be implemented as stand-alone devices deployed within environment 8B.

In general, each of hubs 14 is programmable via SMS 6 so that local alert rules may be installed and executed without requiring a connection to the cloud. As such, each of hubs 14 provides a relay of streams of data from physiological sensors 22, sensing stations 21, beacons 17, and/or PPE 13, and provides a local computing environment for localized alerting based on streams of events in the event communication with SMS 6 is lost.

In example implementations, an environment, such as environment 8B, may also include one or more safety stations 15 distributed throughout the environment. Safety stations 15 may allow one of workers 10 to check out PPE 13 and/or other safety equipment, verify that safety equipment is appropriate for a particular one of environments 8, and/or exchange data. Safety stations 15 may enable workers 10 to send and receive data from physiological sensors 22, sensing stations 21, and/or beacons 17. For example, safety stations 15 may transmit alert rules, software updates, or firmware updates to PPE 13 or other equipment, such as physiological sensors 22, sensing stations 21, and/or beacons 17. Safety stations 15 may also receive data cached on PPE 13, hubs 14, physiological sensors 22, sensing stations 21, beacons 17, and/or other safety equipment. That is, while equipment such as physiological sensors 22, sensing stations 21, beacons 17, PPE 13, and/or data hubs 14 may typically transmit data via network 4 in real time or near real time, such equipment may not have connectivity to network 4 in some instances, situations, or conditions. In such cases, physiological sensors 22, sensing stations 21, beacons 17, PPE 13, and/or data hubs 14 may store data locally and transmit the data to safety stations 15 upon regaining connectivity to network 4. Safety stations 15 may then obtain the data from physiological sensors 22, sensing stations 21, beacons 17, PPE 13, and/or data hubs 14.

In addition, each of environments 8 may include computing facilities that provide an operating environment for end-user computing devices 16 for interacting with SMS 6 via network 4. For example, each of environments 8 typically includes one or more safety managers responsible for overseeing safety compliance within the environment. In general, each user 20 interacts with computing devices 16 to access SMS 6. Each of environments 8 may include systems. Similarly, remote users may use computing devices 18 to interact with SMS 6 via network 4. For purposes of example, the end-user computing devices 16 may be laptops, desktop computers, mobile devices such as tablets or so-called smart phones and the like.

Users 20, 24 interact with SMS 6 to control and actively manage many aspects of safety equipment utilized by workers 10, such as accessing and viewing usage records, analytics and reporting. For example, users 20, 24 may review usage data acquired and stored by SMS 6, where the usage data may include data specifying starting and ending times over a time duration (e.g., a day, a week, etc.), data collected during particular events, such as lifts of a PPE 13 visor, removal of PPE 13 from a worker 10, changes to operating parameters of PPE 13, status changes to components of PPE 13 (e.g., a low battery event), motion of workers 10, detected impacts to PPE 13 or hubs 14, sensed data acquired from the user, environment data, and the like. In addition, users 20, 24 may interact with SMS 6 to perform asset tracking and to schedule maintenance events for individual pieces of safety equipment, e.g., PPE 13, to ensure compliance with any procedures or regulations. SMS 6 may allow users 20, 24 to create and complete digital checklists with respect to the maintenance procedures and to synchronize any results of the procedures from computing devices 16, 18 to SMS 6.

Further, SMS 6 may integrate an event processing platform configured to process thousand or even millions of concurrent streams of events from digitally enabled devices, such as physiological sensors 22, sensing stations 21, beacons 17, PPE 13, and/or data hubs 14. An underlying analytics engine of SMS 6 may apply historical data and models to the inbound streams to compute assertions, such as identified anomalies or predicted occurrences of safety events based on conditions or behavior patterns of workers 10. In general, a safety event may refer to activities of a user of personal protective equipment (PPE), a safety condition of the PPE, or a hazardous environmental condition. For example, in the context of hearing, vision, or head protection equipment, a safety condition may be such protection equipment being in a standby configuration. In the context of hazardous equipment, a safety condition may be proximity of a worker to the hazardous equipment.

Further, SMS 6 may provide real-time alerting and reporting to notify workers 10 and/or users 20, 24 of any predicted events, anomalies, trends, and the like. The analytics engine of SMS 6 may, in some examples, apply analytics to identify relationships or correlations between sensed worker data, environmental conditions, geographic regions and other factors and analyze the impact on safety events. SMS 6 may determine, based on the data acquired across populations of workers 10, which particular activities, possibly within certain geographic region, lead to, or are predicted to lead to, unusually high occurrences of safety events.

In this way, SMS 6 tightly integrates comprehensive tools for managing personal protective equipment with an underlying analytics engine and communication system to provide data acquisition, monitoring, activity logging, reporting, behavior analytics and alert generation. Moreover, SMS 6 provides a communication system for operation and utilization by and between the various elements of system 2. Users 20, 24 may access SMS 6 to view results on any analytics performed by SMS 6 on data acquired from workers 10. In some examples, SMS 6 may present a web-based interface via a web server (e.g., an HTTP server) or client-side applications may be deployed for devices of computing devices 16, 18 used by users 20, 24, such as desktop computers, laptop computers, mobile devices such as smartphones and tablets, or the like.

In some examples, SMS 6 may provide a database query engine for directly querying SMS 6 to view acquired safety data, compliance data and any results of the analytic engine, e.g., by the way of dashboards, alert notifications, reports and the like. That is, users 20, 24 or software executing on computing devices 16, 18, may submit queries to SMS 6 and receive data corresponding to the queries for presentation in the form of one or more reports or dashboards. Such dashboards may provide various insights regarding system 2, such as baseline ("normal") operation across worker populations, identifications of any anomalous workers engaging in abnormal activities that may potentially expose the worker to risks, identifications of any geographic regions within environments 8 for which unusually anomalous (e.g., high) safety events have been or are predicted to occur, identifications of any of environments 8 exhibiting anomalous occurrences of safety events relative to other environments, and the like.

As illustrated in detail below, SMS 6 may simplify workflows for individuals charged with monitoring and ensure safety compliance for an entity or environment. That is, SMS 6 may enable active safety management and allow an organization to take preventative or correction actions with respect to certain regions within environments 8, particular pieces of safety equipment or individual workers 10, define and may further allow the entity to implement workflow procedures that are data-driven by an underlying analytical engine.

As one example, the underlying analytical engine of SMS 6 may be configured to compute and present customer-defined metrics for worker populations within a given environment 8 or across multiple environments for an organization as a whole. For example, SMS 6 may be configured to acquire data and provide aggregated performance metrics and predicted behavior analytics across a worker population (e.g., across workers 10 of either or both of environments 8A, 8B). Furthermore, users 20, 24 may set benchmarks for occurrence of any safety incidences, and SMS 6 may track actual performance metrics relative to the benchmarks for individuals or defined worker populations.

As another example, SMS 6 may further trigger an alert if certain combinations of conditions are present, e.g., to accelerate examination or service of a safety equipment, such as one of PPE 13. In this manner, SMS 6 may identify individual PPE 13 or workers 10 for which the metrics do not meet the benchmarks and prompt the users to intervene and/or perform procedures to improve the metrics relative to the benchmarks, thereby ensuring compliance and actively managing safety for workers 10.

In accordance with techniques of this disclosure, SMS 6 may manage risks to a worker operating within or being considered for operating within an environment based on based at least in part the physiological characteristics of worker 10A and a risk profile associated with worker 10A.

For example, SMS 6 may perform predictive analytics to manage risks to workers 10 prior to entering a physical environment 8 and/or while working in a physical environment 8. In some examples, SMS 6 may evaluate risk to a particular worker (e.g., worker 10A) based at least in part on physiological characteristics (e.g., heart rate, breathing rate, body temperature, etc.) detected by one or more sensors 22 for the particular worker 10A. For example, SMS 6 may receive an indication of the current heart rate of worker 10A and may compare the heart rate to a threshold heart rate. In some examples, SMS 6 may determine that the heart rate of worker 10A has exceeded the threshold heart rate for a threshold amount of time (e.g., 20 minutes), exceeds the threshold heart rate by a threshold amount (e.g., 30%), or has exceeded the threshold heart rate by a threshold amount for the threshold amount of time, and in response, may determine that worker 10A is at high risk.

As another example, SMS 6 may compute a safety risk score for a worker based at least in part the physiological characteristics of workers 10A and a risk profile 25 associated with worker 10A. In some examples, risk profile 25 includes historical physiological data indicative of historical physiological characteristics of worker 10A, biographical data (e.g., demographic data, work experience or training, etc.) for worker 10A and/or other workers, physiological data indicative of historical physiological characteristics (e.g., current and/or historical physiological characteristics) of other workers, environmental data (e.g., air temperature, humidity, ambient light, etc.), equipment data (e.g., type of equipment, insulation performance of the equipment, etc.), or any combination therein.

SMS 6 may determine the safety risk score for worker 10A based on one or more rules. In some instances, the rules may be preprogrammed. As another example, the one or more rules may be generated by at least one model using machine learning. The at least one model may receive an indication of one or more current physiological characteristics of worker 10A and a risk profile 25 as inputs and may output an indication of the safety risk score for worker 10A.

In some examples, SMS 6 determines the safety risk score for worker 10A based on current physiological characteristics of worker 10A and a risk profile 25 that includes historical physiological data indicative of historical physiological characteristics of worker 10A. For example, SMS 6 may receive current physiological data for worker 10A indicating a value of a particular physiological characteristic (e.g., heart rate) of worker 10A. As one example, SMS 6 may receive an indication that the heart rate of worker 10A is currently 160 beats per minute. SMS 6 may determine, based on historical physiological data for worker 10A, that the heart rate of worker 10A is within a normal range for worker 10A when working within environment 8A. In such examples, SMS 6 may assign a relatively low (e.g., 10 out of 100) safety risk score to worker 10A. In another example, SMS 6 may receive an indication that the heart rate of worker 160 is 160 beats per minute and that the breathing rate of worker 10A is 30 breaths per minute. SMS 6 may determine based on the historical physiological data for worker 10A that the heart rate of worker 10A is within a normal range for worker 10A but that the breathing rate of worker 10A is not within a normal rage. In such examples, SMS 6 may assign a relatively high (e.g., 50 out of 100) safety risk score to worker 10A.

As used herein, the safety risk score for a worker may refer to an absolute score, a rank or other relative positioning within a group of workers, a classification (e.g., "Low risk", "Medium risk", "High risk"), or other value usable for assessing the risk to a worker among a group of workers for subsequent operating within an environment.

SMS 6 may determine the safety risk score for 10A based at least in part on a risk profile 25 that includes data associated with one or more workers that are similar to worker 10A. In some examples, the data associated with workers similar to worker 10A, also referred to as similar workers, may include physiological data (e.g., current and/or historical physiological data) for the similar workers, biographical data for the similar workers, or a combination therein. For example, SMS 6 may determine the safety risk score for worker 10A based at least in part on the current physiological data for worker 10A and physiological data for one or more similar workers.

In some examples, SMS 6 determines or identifies a group of one or more workers similar to worker 10A. SMS 6 may determine, based on the risk profile associated with worker 10A, a worker classification for worker 10A and determine a group of similar workers based on the worker classification. For example, the risk profile associated with worker 10A may indicate worker biographical data (e.g., demographic data, work experience or training data, and the like). In other words, SMS 6 may classify worker 10A based on location data, task data, worker biographical data, and the like as indicated in the risk profile associated with worker 10A, and determine the group of similar workers based on the worker classification. Task data may include a type of job or task to be performed (e.g., welding, painting, etc.). Location data may include a geographical area (e.g., city, street address, etc.) or type of environment (e.g., warehouse, medical office, etc.) a task is to be performed in. Worker biographical data may include worker demographic data, training and/or experience data, or the like. In the example of FIG. 1, SMS 6 may determine that the group of workers similar to worker 10A include workers in the same or similar environment as worker 10A. For example, SMS 6 may determine that the group of workers similar to worker 10A, also referred to as the group of similar workers, includes workers 10B, 1° C. because workers 10A-10C are all working in the same environment 8B. In some examples, the group of similar workers includes additional workers in a same or similar type of environment as environment 8B. In some examples, SMS 6 identifies a group of workers (e.g., workers 10D-10E) that are similar to worker 10A based on worker biographical data, for example, by determining workers with same or similar demographic data, workers performing same or similar tasks, workers with same or similar work experience or training, or any combination therein. As illustrated in Table 1, in some examples, SMS 6 may determine that workers 10B-10E are similar to worker 10A, for example, based on the environment workers 10A-10E are assigned to work.

TABLE 1

| Worker | Environment | Environment Temp | 15 Min Activity | 30 Min Activity | 15 Min Heart High | 15 Min Heart Low | 15 Min Skin Temp | 15 Min Ear Temp | Humidity |
|---|---|---|---|---|---|---|---|---|---|
| 10A | Boiler Rm | 92 | Low | Low | 127 | 125 | 91 | 101 | Low |
| 10B | Boiler Rm | 92 | Low | Low | 92 | 82 | 93 | 98 | Low |
| 10C | Boiler Rm | 92 | Low | Low | 80 | 78 | 90 | 98 | Low |
| 10D | Break | 72 | High | High | 150 | 133 | 89 | 98 | Low |
| 10E | Break | 72 | Low | Low | 65 | 54 | 85 | 100 | Low |

Responsive to determining a group of workers (e.g., 10B-10E) that are similar to worker 10A, SMS 6 may, in some examples, determine the safety risk score for worker 10A based at least in part on the physiological data for worker 10A and the physiological data associated with the group of workers similar to worker 10A (e.g., workers in the same or similar environment). In some examples, the physiological data for the group of similar workers includes current physiological data generated by physiological sensors at approximately the same time as the current physiological data generated by sensor 22A associated with worker 10A. As used throughout this disclosure, a "time" refers to a period of time, such as a minute, several minutes, an hour, etc., rather than an instant in time. For example, SMS 6 may receive data indicating the current heart rate of worker 10A is 160 beats per minute, the current heart rate of worker 10B is 120 beats per minute, and the current heart rate of worker 10C is 113 beats per minute. In such examples, SMS 6 may determine or assign a relatively high (e.g., 75 out of 100) safety risk score to worker 10A because the current heart rate of worker 10A is outside a normal range of current heart rates for the similar workers 10B, 1° C.

As another example, SMS 6 may receive historical physiological data generated by physiological sensors 22B, 22C worn by respective workers 10B, 10C. The historical physiological data may include data generated by physiological sensors at a time earlier than the current time (e.g., a previous workday). For example, worker 10A may be working alone and the current physiological data for worker 10A may indicate that the current breathing rate for worker 10A is 20 breaths per minute. SMS 6 may query historical physiological data for similar workers (e.g., workers who have previously performed a similar task) and determine that the breathing rate for similar workers (e.g., while performing similar tasks) is typically between 18 and 22 breaths per minute. In such examples, SMS 6 may determine the safety risk score for worker 10A is relatively low (e.g., 25 out of 100).

In some examples, SMS 6 determines the safety risk score based on data from sensing stations 21. Further, in some such examples, worker 10A utilizes PPE 13A that includes a sensing station 21 and worker 10B utilizes PPE 13B that includes a sensing station 21. SMS 6 may determine whether SMS 6 receives sensor data from the sensing station included in PPE 13. For instance, sensing stations within PPE 13A may be unable to transmit sensor data to SMS 6 due to sensor failure, battery failure, communication failure, etc. Responsive to determining that SMS 6 is not receiving sensor data from a sensing station included in PPE 13A utilized by worker 10A, SMS 6 may determine the safety risk score for worker 10A based on sensor data generated by sensing stations 21 that are included in PPE 13B utilized by worker 10B.

Responsive to determining the safety risk score for worker 10A, SMS 6 may perform one or more operations. In some examples, the one or more operations include outputting a notification indicative of the safety risk score for worker 10A. As one example, SMS 6 may output a notification to one or more of computing devices 16, 18. For example, computing devices 16 located in environment 8B may receive the notification and output (e.g., audibly, graphically, etc.) a notification that includes an indication of the safety risk score for worker 10A. In some examples, the notification may indicate the safety risk score for worker 10A is relatively high and/or indicate that worker 10A should take precautions (e.g., resting) to reduce the safety risk score for worker 10A. As another example, computing devices 18 may receive the notification from SMS 6 and output a notification that includes an indication of the safety risk score for worker 10A to a remote user 24 (e.g., a job site supervisor). In this way, remote users 24 may check-in on worker 10A to intervene (e.g., by removing worker 10A from environment 8B).

In some examples, the notification may include an indication of one or more replacement workers for worker 10A. For example, SMS 6 may identify a group of one or more similar workers (e.g., workers 10D, 10E may have similar work experience and skills as worker 10A) that are not currently working or are working in a different environment and determine whether of workers 10D, 10E are candidates to replace worker 10A. SMS 6 may determine whether workers 10D, 10E are candidates to replace worker 10A by determining that the safety risk scores for workers 10D, 10E are lower (e.g., less than a threshold safety risk score, or more than a threshold difference between the respective safety risk scores) than the safety risk score for worker 10A. In the example of Table 1, SMS 6 may determine that the physiological data for worker 10D indicates worker 10D has a high heart rate and may assign a relatively high safety risk score (e.g., 60 out of 100) to worker 10D, and thus determine that worker 10D is not a replacement for worker 10A. However, SMS 6 may determine, based at least in part on the physiological data for worker 10E, a relatively low safety risk score (e.g., 30 out of 100) for worker 10E. SMS 6 may determine worker 10E is a replacement for worker 10A in response to determining that the safety risk score for worker 10E is less than the safety risk score for worker 10A (e.g., different by a threshold difference in safety risk scores). Thus, SMS 6 may output a notification indicating that worker 10E is a replacement for worker 10A.

In some examples, SMS 6 may output a notification indicative of the safety risk score to a particular article of PPE (e.g., PPE 13A). For example, the notification may indicate the safety risk score for worker 10A is relatively high and/or may include a command to adjust operation of PPE 13A. In some examples, PPE 13A may receive the notification and automatically adjust operation of PPE 13A in response to receiving the notification. For example, the notification may include an indication of the safety risk score for worker 10A, an indication of factors contributing to the safety risk score (e.g., high breathing rate), or a command to increase oxygen flow rate. For example, PPE 13A may increase an oxygen flow rate in response to receiving a notification indicating worker 10A has a high breathing rate.

In some examples, SMS 6 may determine or predict whether worker 10A will experience a safety event based on the safety risk score for worker 10A. For example, the safety risk score may indicate a probability that worker 10A will experience a safety event. In some instances, SMS 6 may predict that worker 10A will experience a safety event in response to determining that the safety risk score for worker 10A satisfies (e.g., is greater than) a threshold safety risk score. In response to predicting that worker 10A will experience a safety event, SMS 6 may output a notification in a similar manner as described above. For example, SMS 6 may output a notification indicating that worker 10A is predicted to experience a safety event to computing devices 16, 18. The notification may include an indication of a replacement worker (e.g., a worker that SMS 6 has predicted will not experience a safety event). In some examples, SMS 6 may output a notification to one or more articles of equipment (e.g., PPE 13) commanding the PPE to automatically adjust operation of the equipment (e.g., increasing oxygen flow rate). In some examples, SMS 6 may automatically output a notification to an emergency response unit (e.g., an emergency dispatch center) indicating worker 10A may require emergency assistance).

In this way, techniques of disclosure enable a safety management system to manage risk to workers operating in, or being considered for operation in, a particular work environment. By determining a safety risk score based on the physiological conditions of a particular worker and a risk profile associated with that worker, the safety management system may tailor the determination of risk for each worker. By tailoring the determination of risk for each worker, the safety management system may more accurately assess risk to workers in various environments. In some examples, the safety management system may output notifications to alert the worker or other individuals (e.g., co-workers, a supervisor) of the safety risk score, which may enable the worker or others (e.g., supervisors) to take action to prevent safety events, thereby increasing worker safety.

Figure 2:
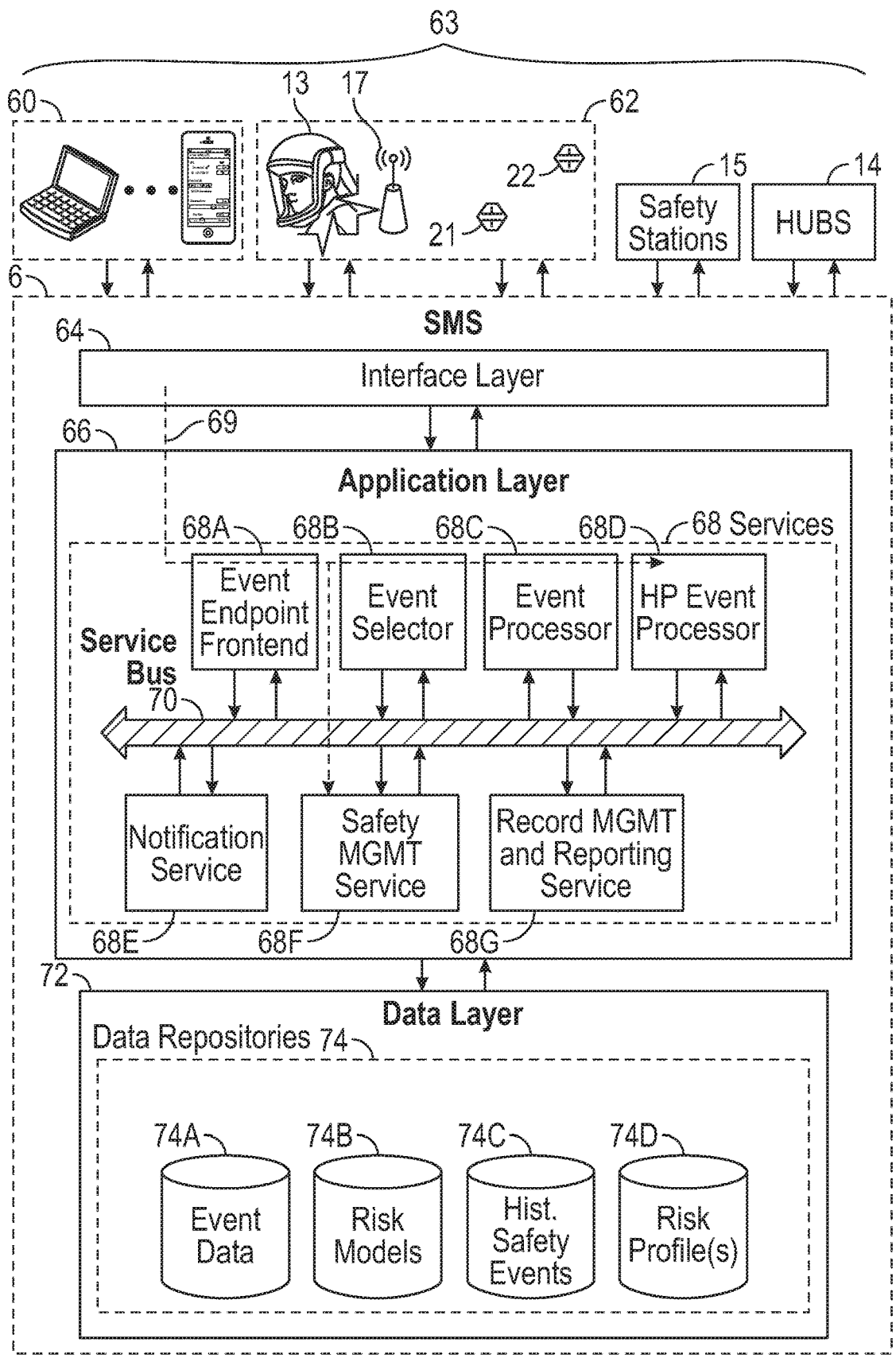
FIG. 2 is a block diagram illustrating, in detail, an operating perspective of the safety management system shown in FIG. 1.

FIG. 2 is a block diagram providing an operating perspective of SMS 6 when hosted as cloud-based platform capable of supporting multiple, distinct environments 8 having an overall population of workers 10, in accordance with techniques described herein. In the example of FIG. 2, the components of SMS 6 are arranged according to multiple logical layers that implement the techniques of the disclosure. Each layer may be implemented by one or more modules comprised of hardware, software, or a combination of hardware and software.

In FIG. 2, safety equipment 62 include personal protective equipment (PPEs) 13, beacons 17, sensing stations 21, physiological sensors 22. Safety equipment 62, HUBs 14, safety stations 15, as well as computing devices 60, operate as clients 63 that communicate with SMS 6 via interface layer 64. Computing devices 60 typically execute client software applications, such as desktop applications, mobile applications, and web applications. Computing devices 60 may represent any of computing devices 16, 18 of FIG. 1. Examples of computing devices 60 may include, but are not limited to a portable or mobile computing device (e.g., smartphone, wearable computing device, tablet), laptop computers, desktop computers, smart television platforms, and servers, to name only a few examples.

Client applications executing on computing devices 60 may communicate with SMS 6 to send and receive data that is retrieved, stored, generated, and/or otherwise processed by services 68. For instance, the client applications may request and edit safety event data including analytical data stored at and/or managed by SMS 6. In some examples, client applications may request and display aggregate safety event data that summarizes or otherwise aggregates numerous individual instances of safety events and corresponding data obtained from safety equipment 62 and/or generated by SMS 6. The client applications may interact with SMS 6 to query for analytics data about past and predicted safety events, behavior trends of workers 10, to name only a few examples. In some examples, the client applications may output for display data received from SMS 6 to visualize such data for users of clients 63. As further illustrated and described in below, SMS 6 may provide data to the client applications, which the client applications output for display in user interfaces.

Clients applications executing on computing devices 60 may be implemented for different platforms but include similar or the same functionality. For instance, a client application may be a desktop application compiled to run on a desktop operating system or a mobile application compiled to run on a mobile operating system. As another example, a client application may be a web application such as a web browser that displays web pages received from SMS 6. In the example of a web application, SMS 6 may receive requests from the web application (e.g., the web browser), process the requests, and send one or more responses back to the web application. In this way, the collection of web pages, the client-side processing web application, and the server-side processing performed by SMS 6 collectively provides the functionality to perform techniques of this disclosure. In this way, client applications use various services of SMS 6 in accordance with techniques of this disclosure, and the applications may operate within various different computing environment (e.g., embedded circuitry or processor of a PPE, a desktop operating system, mobile operating system, or web browser, to name only a few examples).

As shown in FIG. 2, SMS 6 includes an interface layer 64 that represents a set of application programming interfaces (API) or protocol interface presented and supported by SMS 6. Interface layer 64 initially receives messages from any of clients 63 for further processing at SMS 6. Interface layer 64 may therefore provide one or more interfaces that are available to client applications executing on clients 63. In some examples, the interfaces may be application programming interfaces (APIs) that are accessible over a network. Interface layer 64 may be implemented with one or more web servers. The one or more web servers may receive incoming requests, process and/or forward data from the requests to services 68, and provide one or more responses, based on data received from services 68, to the client application that initially sent the request. In some examples, the one or more web servers that implement interface layer 64 may include a runtime environment to deploy program logic that provides the one or more interfaces. As further described below, each service may provide a group of one or more interfaces that are accessible via interface layer 64.

In some examples, interface layer 64 may provide Representational State Transfer (RESTful) interfaces that use HTTP methods to interact with services and manipulate resources of SMS 6. In such examples, services 68 may generate JavaScript Object Notation (JSON) messages that interface layer 64 sends back to the client application 61 that submitted the initial request. In some examples, interface layer 64 provides web services using Simple Object Access Protocol (SOAP) to process requests from client applications 61. In still other examples, interface layer 64 may use Remote Procedure Calls (RPC) to process requests from clients 63. Upon receiving a request from a client application to use one or more services 68, interface layer 64 sends the data to application layer 66, which includes services 68.

As shown in FIG. 2, SMS 6 also includes an application layer 66 that represents a collection of services for implementing much of the underlying operations of SMS 6. Application layer 66 receives data included in requests received from client applications 61 and further processes the data according to one or more of services 68 invoked by the requests. Application layer 66 may be implemented as one or more discrete software services executing on one or more application servers, e.g., physical or virtual machines. That is, the application servers provide runtime environments for execution of services 68. In some examples, the functionality interface layer 64 as described above and the functionality of application layer 66 may be implemented at the same server.

Application layer 66 may include one or more separate software services 68, e.g., processes that communicate, e.g., via a logical service bus 70 as one example. Service bus 70 generally represents logical interconnections or set of interfaces that allows different services to send messages to other services, such as by a publish/subscription communication model. For instance, each of services 68 may subscribe to specific types of messages based on criteria set for the respective service. When a service publishes a message of a particular type on service bus 70, other services that subscribe to messages of that type will receive the message. In this way, each of services 68 may communicate data to one another. As another example, services 68 may communicate in point-to-point fashion using sockets or other communication mechanisms. Before describing the functionality of each of services 68, the layers are briefly described herein.

Data layer 72 of SMS 6 represents a data repository that provides persistence for data in SMS 6 using one or more data repositories 74. A data repository, generally, may be any data structure or software that stores and/or manages data. Examples of data repositories include but are not limited to relational databases, multi-dimensional databases, maps, and hash tables, to name only a few examples. Data layer 72 may be implemented using Relational Database Management System (RDBMS) software to manage data in data repositories 74. The RDBMS software may manage one or more data repositories 74, which may be accessed using Structured Query Language (SQL). Data in the one or more databases may be stored, retrieved, and modified using the RDBMS software. In some examples, data layer 72 may be implemented using an Object Database Management System (ODBMS), Online Analytical Processing (OLAP) database or other suitable data management system.

As shown in FIG. 2, each of services 68A-68J ("services 68") is implemented in a modular form within SMS 6. Although shown as separate modules for each service, in some examples the functionality of two or more services may be combined into a single module or component. Each of services 68 may be implemented in software, hardware, or a combination of hardware and software. Moreover, services 68 may be implemented as standalone devices, separate virtual machines or containers, processes, threads or software instructions generally for execution on one or more physical processors. In some examples, one or more of services 68 may each provide one or more interfaces that are exposed through interface layer 64. Accordingly, client applications of computing devices 60 may call one or more interfaces of one or more of services 68 to perform techniques of this disclosure.

In accordance with techniques of the disclosure, services 68 may include an event processing platform including an event endpoint frontend 68A, event selector 68B, event processor 68C, high priority (HP) event processor 68D, notification service 68E, and safety management services 68F.

Event endpoint frontend 68A operates as a frontend interface for exchanging communications with hubs 14 and safety equipment 62. In other words, event endpoint frontend 68A operates to as a frontline interface to safety equipment deployed within environments 8 and utilized by workers 10. In some instances, event endpoint frontend 68A may be implemented as a plurality of tasks or jobs spawned to receive individual inbound communications of event streams 69 that include data sensed and captured by the safety equipment 62. When receiving event streams 69, for example, event endpoint frontend 68A may spawn tasks to quickly enqueue an inbound communication, referred to as an event, and close the communication session, thereby providing high-speed processing and scalability. Each incoming communication may, for example, carry data recently captured data representing sensed conditions, motions, temperatures, actions or other data, generally referred to as events. Communications exchanged between the event endpoint frontend 68A and safety equipment 62 and/or hubs 14 may be real-time or pseudo real-time depending on communication delays and continuity.

Event selector 68B operates on the stream of events 69 received from safety equipment 62 and/or hubs 14 via frontend 68A and determines, based on rules or classifications, priorities associated with the incoming events. For example, safety rules may indicate that incidents of incorrect equipment for a given environment, incorrect usage of PPEs, or lack of sensor data associated with a worker's vital signs are to be treated as high priority events. Based on the priorities, event selector 68B enqueues the events for subsequent processing by event processor 68C or high priority (HP) event processor 68D. Additional computational resources and objects may be dedicated to HP event processor 68D so as to ensure responsiveness to critical events, such as incorrect usage of PPEs, lack of vital signs, and the like. Responsive to processing high priority events, HP event processor 68D may immediately invoke notification service 68E to generate alerts, instructions, warnings or other similar messages to be output to safety equipment 62, hubs 14, or devices used by users 20, 24. Events not classified as high priority are consumed and processed by event processor 68C.

In general, event processor 68C or high priority (HP) event processor 68D operate on the incoming streams of events to update event data 74A within data repositories 74. In general, event data 74A may include all or a subset of data generated by safety equipment 62. For example, in some instances, event data 74A may include entire streams of data obtained from sensors 22. In other instances, event data 74A may include a subset of such data, e.g., associated with a particular time period.

Event processors 68C, 68D may create, read, update, and delete event data stored in event data 74A. Event data for may be stored in a respective database record as a structure that includes name/value pairs of data, such as data tables specified in row/column format. For instance, a name (e.g., column) may be "worker ID" and a value may be an employee identification number. An event record may include data such as, but not limited to: worker identification, acquisition timestamp(s) and data indicative of one or more physiological characteristics of workers 10. For example, event stream 69 for one or more sensors associated with a given worker (e.g., worker 10A) may be formatted as follows:

{"eventTime":"2015-12-31T18:20:53.1210933Z",
"deviceDataTypeCode":"HEARTBEAT",
"steps": 12402,
"heartrate":70,
"skinTemp":29.37,
"stairs":70,
"galvanicSkinResponse":2996,
"uvRadiation":0,
"DeviceName:":"Jon a4:93"}.

In some examples, event stream 69 include category identifiers (e.g., "eventTime", "DeviceName", "steps", "heartrate", "skinTemp", "stairs", "galvanicSkinResponse", and "uvRadiation", as well as corresponding values for each category.

In some examples, safety management service 68F is configured to perform in depth processing of the incoming stream of events to perform real-time analytics. In this way, stream analytic service 68D may be configured to detect anomalies, transform incoming event data values, trigger alerts upon detecting safety concerns based on conditions or worker behaviors. In addition, stream analytic service 68D may generate output for communicating to safety equipment 62, safety stations 15, hubs 14, or computing devices 60.

In accordance with techniques of this disclosure, safety management service 68F may determine a safety risk score for one or more respective workers of workers 10 based at least in part on events within event stream 69. Safety management service 68F may be configured to determine the safety risk score for worker 10A based at least in part on the sensor data associated with worker 10A and one or more rules. Although other technologies can be used, in some examples, the one or more rules are generated using machine learning. In other words, in one example implementation, safety management service 68F utilizes machine learning when operating on event streams 69 so as to perform real-time analytics. That is, safety management service 68F may include executable code generated by application of machine learning to determine a safety risk score for the worker. The executable code may take the form of software instructions or rule sets and is generally referred to as a model that can subsequently be applied to event streams 69. Example machine learning techniques that may be employed to generate models 74B can include various learning styles, such as supervised learning, unsupervised learning, and semi-supervised learning. Example types of algorithms include Bayesian algorithms, Clustering algorithms, decision-tree algorithms, regularization algorithms, regression algorithms, instance-based algorithms, artificial neural network algorithms, deep learning algorithms, dimensionality reduction algorithms and the like. Various examples of specific algorithms include Bayesian Linear Regression, Boosted Decision Tree Regression, and Neural Network Regression, Back Propagation Neural Networks, the Apriori algorithm, K-Means Clustering, k-Nearest Neighbor (kNN), Learning Vector Quantization (LVQ), Self-Organizing Map (SOM), Locally Weighted Learning (LWL), Ridge Regression, Least Absolute Shrinkage and Selection Operator (LASSO), Elastic Net, and Least-Angle Regression (LARS), Principal Component Analysis (PCA) and Principal Component Regression (PCR).

As further illustrated with reference to FIG. 4, safety management service 68F may utilize machine learning techniques to identify risks that are not necessarily detectable via techniques such as linear regression. For example, safety management service 68F may determine that high levels of movement (e.g., when worker 10A takes a large number of steps) are not related to an increase in risk to worker 10A when analyzed using linear regression techniques, but may determine that high levels of movement are associated with high risk to worker 10A based on clustering techniques (e.g., K-means analysis).

Safety management service 68F may, in some example, generate separate models for a particular worker, a particular population of workers, a particular environment, or combinations thereof. Safety management service 68F may update the models based on physiological sensor data generated by sensors 22. For example, safety management service 68F may update the models for a particular worker, a particular population of workers, a particular environment, or combinations thereof based on physiological data generated by sensors 22.

Safety management service 68F may determine a safety risk score for worker 10A based at least in part by applying one or more risk models 74B to physiological data associated with worker 10A and a risk profile 74D associated with worker 10A. In some examples, risk profile 74D includes physiological data indicative of historical physiological characteristics of worker 10A and/or physiological characteristics (e.g., current and/or historical physiological characteristics) of other workers.

According to one example, safety management service 68F applies one or more of risk models 74B to current physiological data for worker 10A and historical physiological data for worker 10A. In some examples, the physiological data indicates how much worker 10A has sweat over a period of time. For example, safety management service 68F may receive current physiological data from one of sensors 22 (e.g., a sweat sensor) indicating that worker 10A has sweat approximately 0.3 liters of fluid within a predetermined amount of time (e.g., in the last hour) and historical physiological data from risk profiles 74D indicating that worker 10A typically sweats approximately 0.2 liters of fluid within the predetermined amount of time (e.g., while performing a task similar to the task that worker 10A is currently performing and/or in similar weather conditions). Safety management service 68F may determine the safety risk score for worker 10A based on application of one or more risk models 74B to the current physiological data for worker 10A and historical physiological data for worker 10A. For example, safety management service 68F may apply risk models 74B to the amount of sweat from worker 10A within the predetermined amount of time and historical sweat amounts and assign a high (e.g., 60 out of 100) safety risk score for worker 10A.

As another example, safety management service may determine one or more characteristics of a work environment associated with worker 10A. For example, safety management service 68F may determine a type of environment (e.g., warehouse, confined space, refinery, office building, etc.) in which worker 10A is working, or a location of the environment (e.g., address, building number, zipcode, etc.). Safety management service 68F may determine one or more similar work environments and historical physiological data for the worker for the similar work environments.

For instance, safety management service 68F may determine that the work environment is a factory and may determine historical physiological data for worker 10A when worker 10A has worked in factories in the past. In such examples, safety management service 68F may determine the safety risk score for worker 10A based on the current physiological data for worker 10A and historical physiological data that corresponds to worker 10A and the similar environments.

In some examples, safety management service 68F determines a safety risk score for a plurality of workers (e.g. each of workers 10 in environment 8B). Safety management service 68F may determine the safety risk scores for each respective worker of workers 10 based at least in part on current physiological data for each of the workers. In some examples, each worker 10 wears at least one physiological sensor 22 that monitors the physiological characteristics of the respective worker, such that safety management service 68F receives event streams from respective physiological sensors 22 of respective workers 10. Safety management service 68F may apply one or more of models 74B to the physiological data for each respective worker of workers 10 to determine a safety risk score for each respective worker. In other words, safety management service 68F may determine a safety risk score for each worker of the plurality of workers 10.

Safety management service 68F may evaluate or determine a risk associated with each of workers 10A, 10B based at least in part on the physiological data associated with the respective workers 10A, 10B. In other words, safety management service 68F may determine the safety risk score for each worker 10A, 10B. For example, safety management service 68F may apply one or more models 74B to the physiological data associated with respective workers 10A, 10B to determine a safety risk score for workers 10A, 10B. As illustrated by table 2, in some examples, safety management service 68F may determine a category safety risk score for various different categories types of risk for worker 10A and may determine a total safety risk score based at least in part on one or more of the category safety risk scores for worker 10A. For example, safety management service 68F may determine a category safety risk score for a category labeled ActivityLevelRisk at different times throughout the day based on physiological data associated with worker 10A. For example, at time 1, safety management service 68F may receive data from one or more physiological sensors 22 associated with worker 10A indicating that the heart rate and breathing rate of worker 10A over a predetermined amount of time (e.g., the last 10 minutes) is within a normal range (e.g., for worker 10A based on historical physiological data for worker 10A), which may be associated with a relatively low (e.g., 2 out of 5) for the risk category ActivityLevelRisk.

TABLE 2

| Worker Identifier | Location Identifier | Date | Time | Activity-LevelRisk | LackOfRestRisk | TempExposureRisk |
|---|---|---|---|---|---|---|
| 10A | 1 | 2018 Jan. 20 | 1 | 2 | 1 | 1 |
| 10A | 1 | 2018 Jan. 20 | 2 | 1 | 1 | 1 |
| 10A | 5 | 2018 Jan. 20 | 3 | 4 | 1 | 1 |
| 10A | 3 | 2018 Jan. 20 | 4 | 1 | 1 | 1 |
| 10A | 1 | 2018 Jan. 20 | 5 | 5 | 1 | 5 |
| 10A | 1 | 2018 Jan. 20 | 6 | 2 | 1 | 1 |
| 10A | 1 | 2018 Jan. 20 | 7 | 1 | 1 | 1 |
| 10A | 1 | 2018 Jan. 20 | 8 | 1 | 1 | 1 |
| 10B | 4 | 2018 Jan. 20 | 1 | 1 | 1 | 1 |
| 10B | 4 | 2018 Jan. 20 | 2 | 4 | 1 | 1 |
| 10B | 4 | 2018 Jan. 20 | 3 | 1 | 1 | 1 |
| 10B | 4 | 2018 Jan. 20 | 4 | 1 | 1 | 1 |
| 10B | 4 | 2018 Jan. 20 | 5 | 4 | 1 | 5 |
| 10B | 5 | 2018 Jan. 20 | 6 | 5 | 1 | 5 |
| 10B | 5 | 2018 Jan. 20 | 7 | 1 | 1 | 1 |
| 10B | 5 | 2018 Jan. 20 | 8 | 1 | 1 | 1 |

As another example, at time 5, safety management service 68F may determine a category safety IC-1T risk score for a category labeled TempExposureRisk based on current temperature and/or humidity data received from environmental sensors 21, historical temperature and/or humidity data, current physiological data for worker 10A, and historical physiological data for worker 10A and/or other workers. In other words, safety management service 68F may receive an indication of the location temperature and humidity in environment 8B of FIG. 1 and compare the current physiological data for worker 10A to the historical physiological data for workers in environment 8B that worked in environment 8B under similar conditions (e.g., when the current temperature and humidity was similar to or corresponds to historical temperature and humidity information).

Safety management service 68F may determine a risk of worker 10A relative to one or more other workers of workers 10. In other words, the safety risk score for worker 10A may indicate a relative risk to worker 10A compared to risk to one or more other workers. For example, safety management service 68F may determine the risk to worker 10A based on current physiological data for worker 10A and physiological data (e.g., current and/or historical) for one or more other workers. In one instance, event streams 69 may indicate the heart rate (e.g., minimum, maximum, and/or average heart rate) for worker 10A within a predetermined amount of time and the heart rate for one or more other workers 10 within the predetermined amount of time. For instance, event stream 69 may include physiological data indicating the average heart rate for worker 10A is 140 beats per minute and the average heart rate for other workers 10 is 100 beats per minute. In such instances, safety management service may assign a relatively high risk to worker 10A (e.g., "high" on a scale of low, medium, high).

In some examples, safety management service 68F determines a risk for worker 10A relative to a group of one or more similar workers. Safety management service 68F may determine the group of one or more workers by determining a worker classification for worker 10A and determining one or more workers with a corresponding worker classification. In some examples, safety management service 68F determines the worker classification based on the risk profile associated with each respective worker. For example, risk profiles 74D may include biographical data (e.g., demographic data, work experience or training data, etc.) for each worker of workers 10. For example, work experience data may include data indicating an amount of time worker 10A has worked for a company, type of worker (e.g., plumber, electrician, surgeon, etc.), or the like. Training data may include data indicating different types of trainings worker 10A has participated in, skills or certifications acquired by worker 10A, or the like. For instance, safety management service 68F may determine that the work experience for worker 10A is classified as "more than 10 years" and that the type of worker is classified as "electrician." Responsive to determining a worker classification for worker 10A, safety management service 68F may determine a group of one or more similar workers with corresponding worker classifications. Responsive to determining the group of similar workers, safety management service 68F apply one or more of models 74B to physiological data for worker 10A and physiological data (e.g., current or historical) for the group of similar workers to determine the safety risk score for worker 10A.

In some examples, safety management service 68F determines the safety risk score for worker 10A by applying one or more of risk models 74B to current physiological data for worker 10A and historical safety event data. For example, risk profile 74D may include historical physiological data for worker 10A and historical safety events data 74C may include information for previous safety events, such as type of event, location of the event, employees involved (e.g., injured), etc. Risk profile 74D may be associated with (e.g., include a link to) historical sensor data. In some examples, safety management services 68F may apply one or more of models 74B, identify historical events within historical safety events data 74C where a worker experienced physiological conditions similar to the current physiological conditions of worker 10A, and determine the safety risk score for worker 10A based on the identified historical events.

In some examples, the biographical data for worker 10A included in risk profile 74D includes a risk category and corresponding category safety risk scores for each category. In some examples, safety management service 68F may dynamically determine the safety risk score for each risk category. In some examples, the safety risk score for worker 10A for each risk category is predetermined (e.g., determined by an employee safety manager). For example, risk profile 74D may include biographical data as shown in Table 3.

TABLE 3

| Category | Category safety risk score |
|---|---|
| WorkerTaskParticipationRisk | 3 |
| SafetyTrainingRisk | 1 |
| GroupStabilityRisk | 2 |
| TopTalentIdentificationRisk | 4 |
| WorkCommuteDistanceRisk | 1 |
| WorkAbsenceAmountRisk | 1 |
| TaskTenureRisk | 2 |
| PreviousAccidentsRisk | 4 |
| PreviousInjuryRisk | 4 |
| NearMissesRisk | 5 |

As illustrated in Table 3, each category indicates a type of risk and the corresponding category safety risk score indicates a degree of risk for worker 10A, where a category safety risk score of 1 indicates a low level of risk and a category safety risk score of 5 indicates a high level of risk. In the example shown in Table 3, the category safety risk score associated with WorkParticipationRisk for worker 10A corresponds to a medium level (e.g., 3 of 5) of risk. For example, worker 10A may be an unreliable attendee at meetings and trainings, where low attendance may be correlated to a higher accident rate. Worker 10A may be associated with a low SafetyTrainingRisk (e.g., 1 out of 5), for example, because worker 10A reliably attends trainings. As further illustrated in Table 3, worker 10A may be associated with a high (e.g., 4 out of 5) PreviousAccidentsRisk and high (e.g., 4 out of 5) PreviousInjuryRisk, for example, due to an accident involving an injury within a predefined amount of time (e.g., within the previous three months).

In some examples, a distance from the workers home to the work environment may be indicative of worker risk. For example, shorter commutes may correspond to higher risk because workers who live close to work may rush to work at the last minute and may not be fully alert. As another example, workers with too long of commutes may correspond to higher risk with very long commutes may become drowsy. The category WorkCommuteDistanceRisk may indicate risk to the worker based on distance from the workers home to the work environment. In the example of table 3, worker 10A may be associated with a low safety risk score for the category WorkCommuteDistanceRisk.

In some examples, risk profiles 74D may include a task risk profile indicative of one or more tasks to be performed (e.g., type of task). In some examples, the task risk profile may include task data associated with various tasks, where the task data is the same for all workers for a particular task and/or environment. In other words, if a task includes working in confined spaces, the task risk profile may indicate the risk is the same for all workers who work in the confined spaces. In another example, the task risk profile include individualized data, such that a first worker may be associated with a high risk for a particular task relative to a different worker for the same task. In some examples, the task ranking may be completed by a certified safety officer in accordance with an approved OSHA ranking methodology.

Table 4 illustrates a task risk profile within risk profiles 74D that includes risk categories and corresponding category risks scores for a particular task or task:

TABLE 4

| TaskIdentifer | TaskRisk | RecentNearMiss | RecentAccidentRisk |
|---|---|---|---|
| 3 | 5 | 5 | 5 |

As illustrated by Table 4, the task associated with TaskIdentifier 3 may be a high-risk task. For example, task 3 may be rated relatively high because the task may be physically dangerous and there may have been recent accidents.

Table 5 illustrates a task risk profile for a different task:

TABLE 5

| TaskIdentifer | TaskRisk | RecentNearMiss | RecentAccidentRisk |
|---|---|---|---|
| 1 | 3 | 1 | 1 |

As illustrated in Table 5, the task associated with TaskIdentifier 1 may be a medium risk task and there have not been any recent near misses and no recent accidents associated with task 1.

Safety management service 68F may receive an indication of the task to be performed by worker 10A (e.g., as identified by the TaskIdentifier) and determine the risk for worker 10A by applying one or more of models 74B to the task risk profile associated with the task to be performed.

In some examples, risk profiles 74D include environmental data that is generated by one or more sensors 21 and is indicative of characteristics of a particular environment 8 (e.g., air temperature, humidity, ambient light, noise levels, radiation, air quality, chemical exposure, visibility, etc.). For example, SMS 6 may receive environmental data from one or more sensors 21. Safety management service 68F may apply one or more of models 74B to the environmental data to determine a risk for worker 10A (e.g., when worker 10A is working in, or is scheduled to begin working in, environment 8B). For example, safety management service 68F may assign a higher safety risk score to worker 10A as the air temperature increases above a threshold temperature (e.g., 100 degrees Fahrenheit). In some examples, risk profiles 74D include additional environmental data, such as data indicating a location of the environment (e.g., lat/long coordinates, address, city, zipcode, etc.), type of environment (e.g., hospital, factory, warehouse, etc.), and the like.

In some examples, risk profiles 74D include an indication of risk for various environmental factors associated with a particular environment. Table 6 illustrates environment data corresponding to an example location. For example, as illustrated in table 6, the location corresponding to LocationIdentifier category safety risk score of 1 has a relatively high TemperatureRisk (e.g., 4 out of 5), a relatively low HumidityRisk (e.g., 1 out of 5) and WeatherRisk (e.g., 1 out of 5).

TABLE 6

| LocationIdentifier | Temperaturerisk | HumidityRisk | WeatherRisk |
| --- | --- | --- | --- |
| 1 | 4 | 1 | 1 |

In examples where worker 10A is working at or is being considered to work at the location corresponding to a LocationIdentifier of 1, safety management service 68F may determine a safety risk score for worker 10A is relatively low (e.g., 1 out of 5, 15 out of 100, etc.) based on applying one or more of models 74B to environmental data within risk profiles 74D.

Risk profiles 74D may include equipment data indicative of one or more articles of equipment. For example, risk profiles 74D may include equipment data for one or more articles of PPE (e.g., type of equipment, insulation performance of the equipment, indication of remaining lifespan for an article of equipment, such as battery life or filter life, etc.) or other equipment that may be utilized by worker 10A to perform a task. In some examples, safety management service 68F determines the safety risk score for worker 10A by applying one or more of models 74B to the equipment data generated by equipment utilized by worker 10A while performing a given task.

In some examples, safety management service 68F may determine whether to worker 10A is qualified or an otherwise appropriate worker to perform a particular task or work in a particular environment based on a total safety risk score for worker 10A. For example, safety management service 68F may determine a total safety risk score for worker 10A based on an average safety risk score for one or more category safety risk scores, and may determine whether worker 10A is an appropriate worker by comparing the total safety risk score to a threshold safety risk score.

As another example, safety management service 68F may determine whether worker 10A is an appropriate worker for a particular task or environment based on the separate category safety risk scores. In other words, safety management service 68F may compare one or more category safety risk score to respective threshold safety risk score to determine whether worker 10A is an appropriate worker. For example, safety management service 68F may determine that worker 10A is not appropriate in response to determining that the safety risk score for worker 10A for the risk category SafetyTrainingRisk satisfies (e.g., is greater than or equal to) a threshold safety risk score. Such an example may indicate that worker 10A is not up to date on his or her trainings. As another example, safety management service 68F may determine that worker 10A is not an appropriate worker for a particular task and/or particular environment in response to determining that the category safety risk score for worker 10A for the risk category WorkerTaskParticipationRisk satisfies (e.g., is equal to or greater than) a first threshold safety risk score and that the category safety risk score for worker 10A for the risk category SafetyTrainingRisk also satisfies a second threshold safety risk score (e.g., which may be the same or different than the first threshold safety risk score). Such an example may indicate that worker 10A is not up to date on their training and is not participating appropriately in update meetings. As yet another example, safety management service 68F may determine that worker 10A is not an appropriate worker for an early morning task in response to determining that the category safety risk score for worker 10A for the risk category WorkCommuteDistanceRisk satisfies the threshold safety risk score, for example, because workers with a relatively high safety risk score for the risk category WorkCommuteDistanceRisk may not be fully alert early in the morning.

In some examples, safety management service 68F may update or re-train one or more models 74B. Safety management service 68F may update one or more models 74B based on additional physiological data. In other words, safety management service 68F may update risk factors that are already identified and/or identify new risk factors previously undiscovered to aid in the prediction of near misses and accidents so that those risk factors can be reduced. As another example, safety management service 68F may receive data from other sources, such as safety organizations (e.g., OSHA), and may update one or more models 74B based on the other data sources to identify potential collective improvements for worker safety. For example, other data sources may include an accident and near miss database for the mining industry or an accident database for the chemical industry.

In some examples, safety management service 68F determines the safety risk score for one or more of workers 10 on a periodic basis. For example, safety management service 68F may determine the safety risk score for workers 10 on a regular schedule (e.g., daily, hourly, etc.). Safety management service 68F may determine the safety risk scores on demand. For example, safety management service 68F may determine the risk respective scores for one or more workers 10 in response to receiving a query from one of computing devices 60 indicating a request for a safety risk score for the one or more workers. As another example, safety management service 68F may determine the safety risk score for one or more workers 10 in response to receiving a query indicating a request to identify one or more low risk workers.

Safety management service 68F may output an indication of the safety risk score for one or more workers 10. In some examples, safety management service 68F may output a notification that includes the safety risk score. As another example, in response to receiving a request to identify one or more low risk workers, safety management service 68F may determine the respective safety risk scores of one or more workers and may output information identifying the one or more low risk workers. As yet another example, safety management service 68F may receive a request to identify one or more workers who are high risk, determine the safety risk scores for one or more workers, and output information identifying one or more high risk workers.

In some examples, safety management service 68F may predict whether worker 10A will experience a safety event based at least in part on the safety risk score for worker 10A. For example, the safety risk score may be indicative of a probability the worker will experience a safety event. In some instances, a safety event may include a heat related illness or injury, a cardiac related illness or injury, a respiratory illness or injury, or a hearing related illness or injury. Safety management service 68F may compare the safety risk score for worker 10A to a threshold safety risk score and may predict that worker 10A will experience a safety event in response to determining that the safety risk score for worker 10A satisfies (e.g., is greater than or equal to) the threshold safety risk score.

In response to predicting that worker 10A will experience a safety event, safety management service 68F may output a notification indicating worker 10A is predicted to experience a safety event. In some examples, the notification includes a message indicating the identify of worker 10A, a location of worker 10A, etc. In some examples, the notification includes information identifying at least one replacement worker that is not predicted to experience a safety event. In some examples, safety management service 68F may a notification to at least one article of personal protective equipment utilized by worker 10A in response to predicting that the worker will experience the safety event. For example, the notification may include a command to adjust operation of the at least one article of personal protective equipment.

Figure 3:
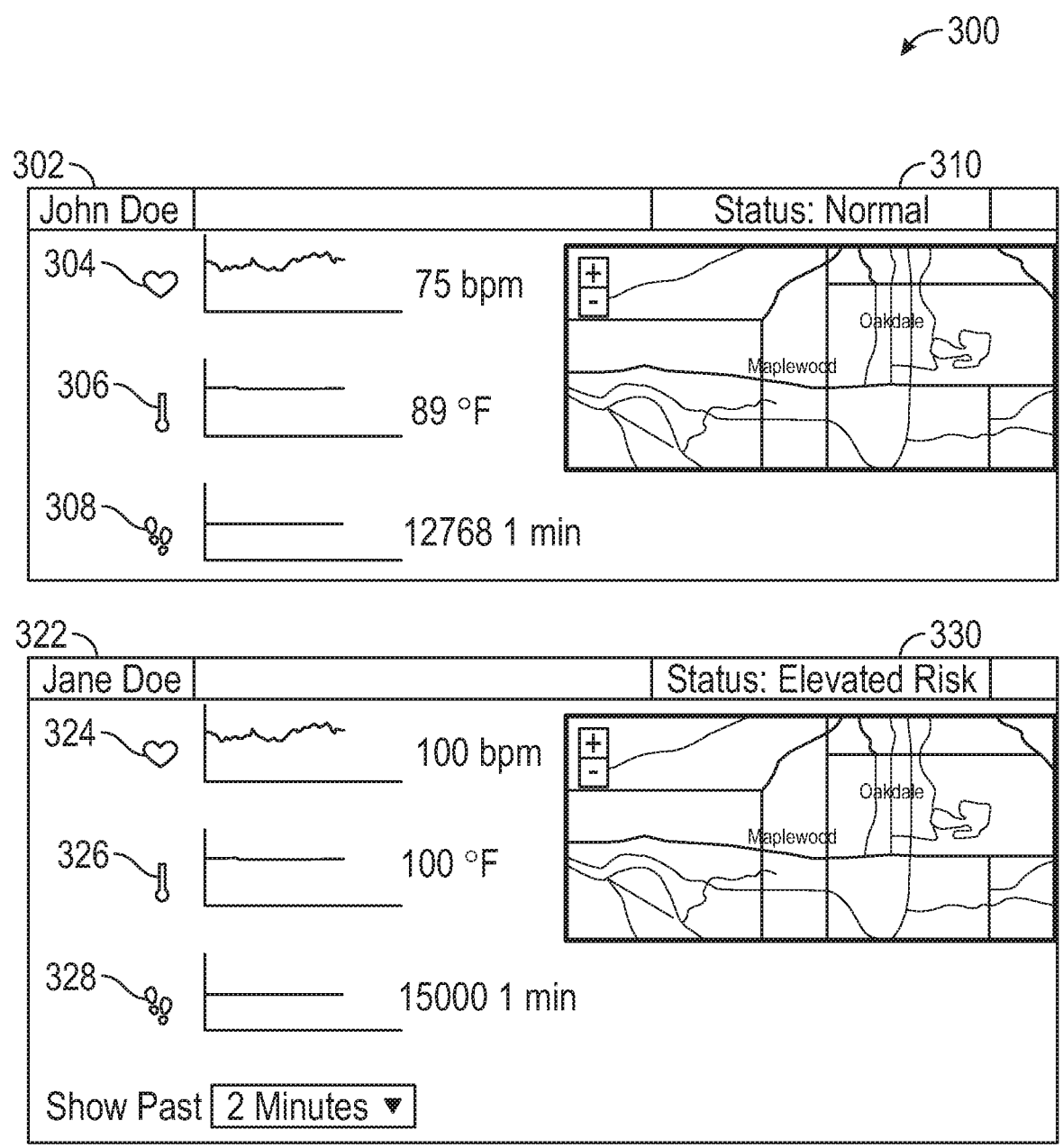
FIG. 3 illustrates an example user interface of the worker safety management system, according to techniques of this disclosure.

FIG. 3 illustrates an example user interface for a worker safety management system, according to techniques of this disclosure. For example, SMS 6 of FIGS. 1 and 2 may determine a safety risk score for one or more workers 10. As illustrated in the example of FIG. 3, user interface 300 includes physiological data associated with a first worker 302 named John Doe and a second worker 322 named Jane Doe. Graphical user interface 300 includes physiological data for such as heart rate 304, temperature 306, and step count 308 for worker 302 and heart rate 324, temperature 326, and step count 328 for worker 322. Graphical user interface 300 may include an indication of the safety risk score for each of workers 302, 322. For example, as illustrated in FIG. 3, graphical user interface 300 includes a graphical element (e.g., a text box, image, etc.) 310 indicating the safety risk score for worker 302 and a graphical element 330 indicating the safety risk score for worker 322. In the example of FIG. 3, graphical user interface 300 indicates that the safety risk score for worker 302 indicates the risk for worker 302 is a normal level and that the safety risk score for worker 322 is elevated. In this way, SMS 6 may output a notification (e.g., to computing devices 60 of FIG. 2) indicating that worker 322, which may enable a safety manager to assist worker 322 and/or remove worker 322 from the work environment.

Figure 4:
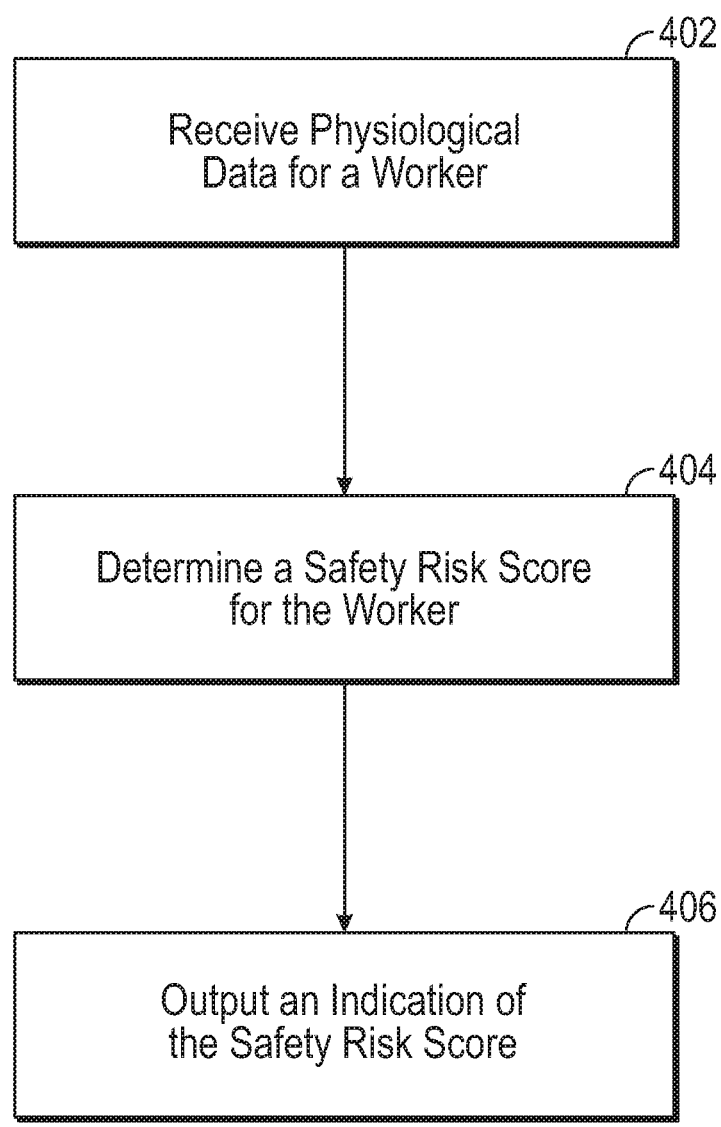
FIG. 4 is a flowchart illustrating an example mode of operation for a worker safety management system, according to techniques described in this disclosure.

FIG. 4 is a flowchart illustrating an example mode of operation for a worker safety management system, according to techniques described in this disclosure. SMS 6 may receive physiological data that is generated by one or more physiological sensors and is indicative of one or more physiological characteristics of a worker 10A (402). In some examples, the physiological sensors include a heart rate sensor, breathing sensor, sweat sensor, galvanic skin response sensor, temperature sensor, etc. SMS 6 may receive the physiological data (e.g., the raw sensor data, a summary of the sensor data, or a subset of the sensor data) directly from one or more physiological sensors or indirectly (e.g., via hub 14).

In some examples, SMS 6 determines a safety risk score for worker 10A based at least in part on the physiological data for worker 10A and a risk profile associated with worker 10A (404). The risk profile associated with worker 10A may include historical physiological data for worker 10A, biographical data (e.g., demographic data, work experience data) for worker 10A, physiological data (e.g., current and/or historical) for other workers, etc. In some examples, the risk profile associated with worker 10A includes a task risk profile associated with a task to be performed by worker 10A, an environmental risk profile associated with the environment in which worker 10A is working, etc.

In some examples, SMS 6 outputs an indication of the safety risk score for worker 10A (406). SMS 6 may output a notification to one or more computing devices 60. For instance, as illustrated in FIG. 3, the notification may include the safety risk score for one or more workers or include an indication of the safety risk score (e.g., "low", "normal", "elevated") for the one or more workers. In some instance, SMS 6 outputs the notification to one or more articles of equipment (e.g., an article of PPE) in the work environment to provide worker 10A or other workers in the environment of the risk to one or more workers. The notification may include a message indicating whether worker 10A is an appropriate worker for a given task or work environment. In some examples, the message indicates an alternative or replacement worker who is an appropriate worker for the given task or work environment.

Figure 5:
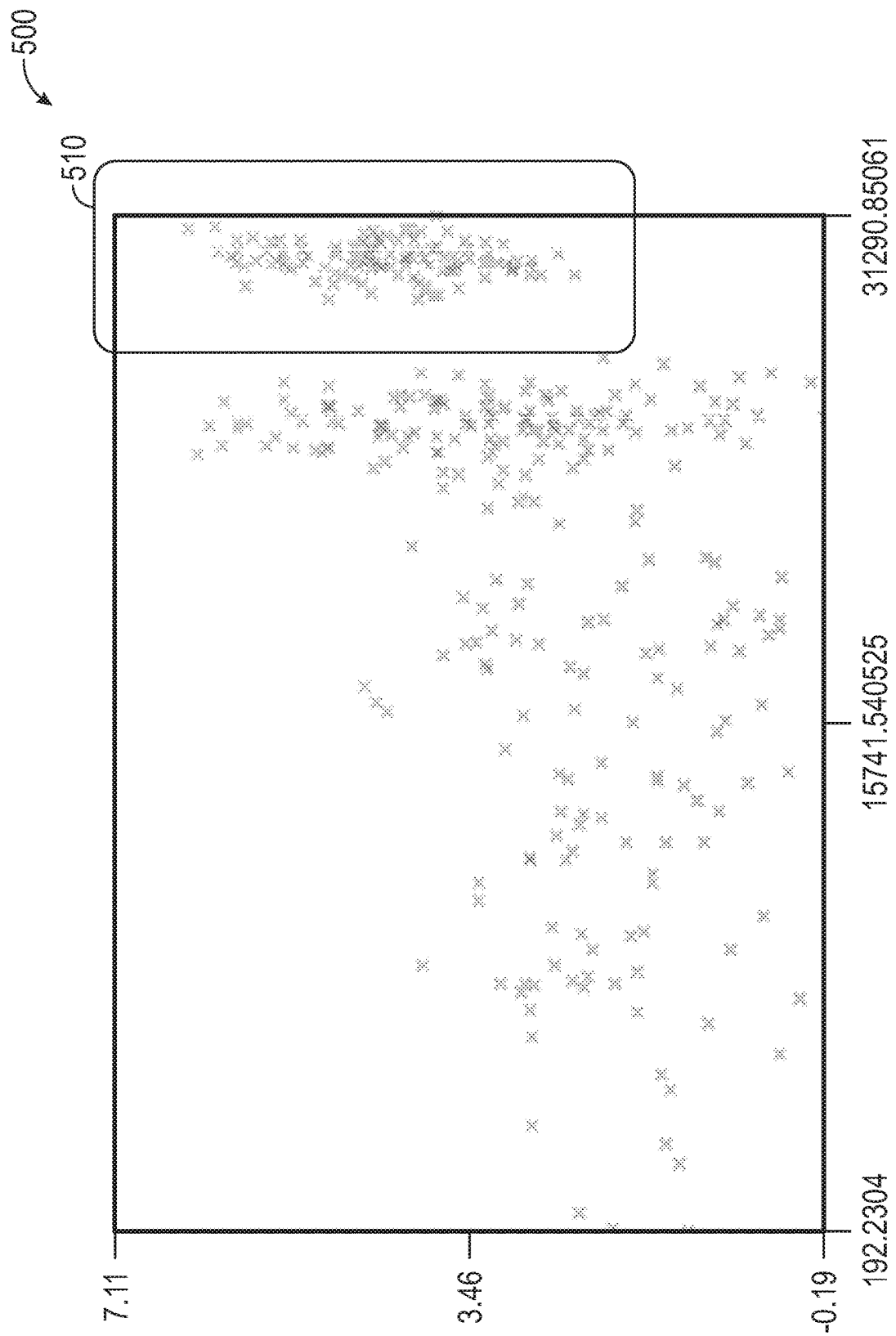
FIG. 5 is diagram illustrating an example risk analysis based on a clustering algorithm, according to techniques described in this disclosure.

FIG. 5 is diagram illustrating an example risk analysis based on a clustering algorithm, according to techniques described in this disclosure. The x-axis of scatter diagram 500 illustrates a number of daily steps taken by workers 10 and the y-axis of scatter diagram 500 illustrates a daily risk for workers 10. Linear regression techniques may not indicate that the number of steps taken by a given worker is associated with risk to the worker. Safety management service 68F of FIG. 2 may perform machine learning techniques, such as a clustering (e.g., K-means) algorithm on worker daily step count and worker daily risk. As illustrated in FIG. 5, the clustering analysis may indicate the risk to workers 10 is associated with daily step count. For instance, region 510 of scatter diagram 500 indicates that high levels of movement are associated with high risk to worker 10A.

Figure 6:
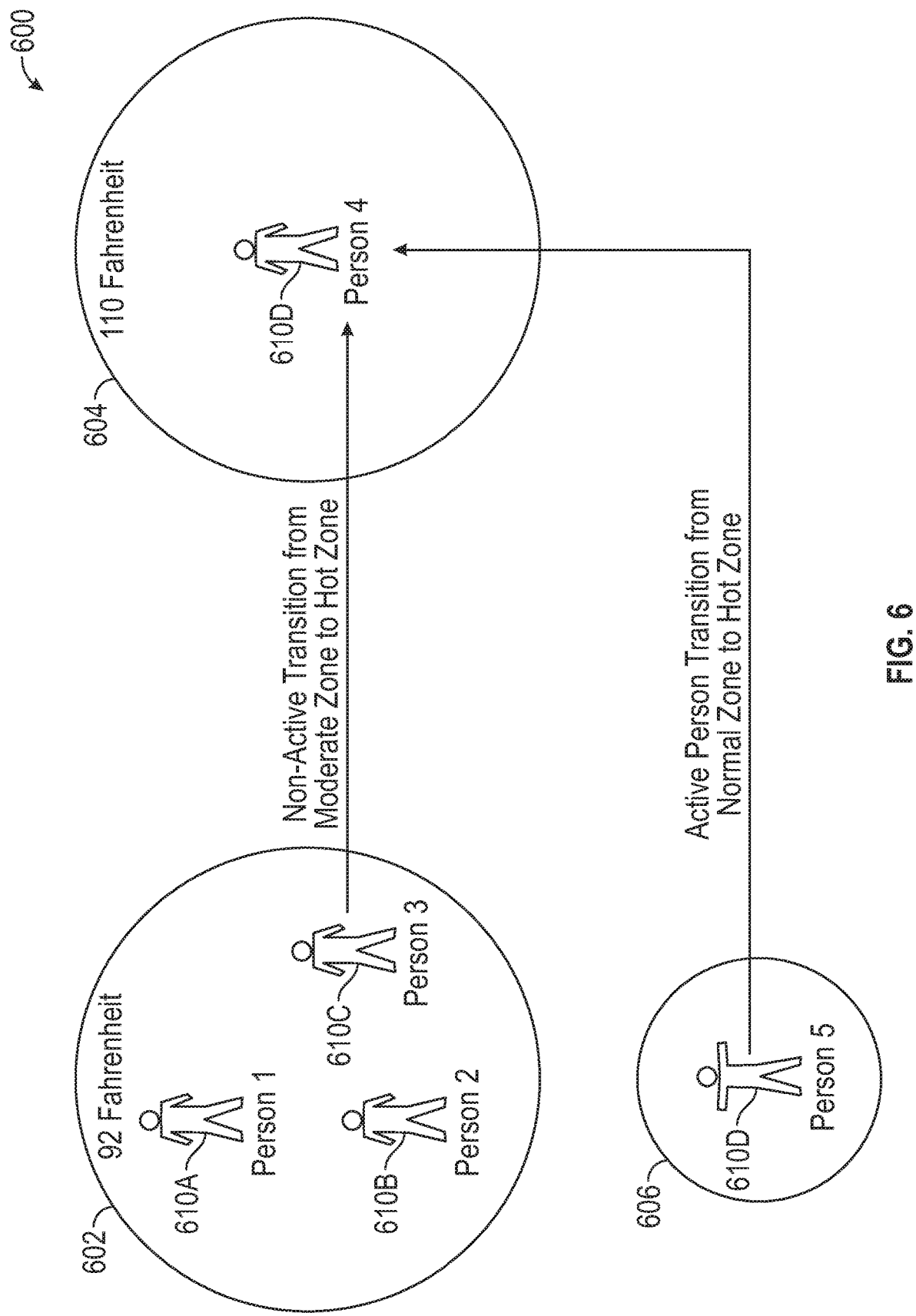
FIG. 6 is a conceptual diagram illustrating operation of the worker safety management system, according to aspects of this disclosure.

FIG. 6 is a conceptual diagram illustrating operation of the worker safety management system, according to aspects of this disclosure. FIG. 6 is described with reference to worker safety management system 6 as described in FIGS. 1 and 2.

System 600 includes a plurality of environments 602, 604, and 606. Environments 602, 604, and 606 may be examples of any of environments 8 described with reference to FIG. 1. In the example of FIG. 6, environment 602 includes workers 610A, 610B, and 610C, environment 604 includes worker 610D, and environment 606 includes worker 610D.

SMS 6 may receive physiological data associated with workers 610. For example, SMS 6 may receive heart rate data, skin temperature data, and ear temperature data for each of workers 610. SMS 6 may also receive environmental data associated with environments 602, 604, and 606. For example, SMS 6 may receive environment temperature data and environment humidity data. In some examples, SMS 6 may receive data generated by one or more motion sensors associated with one or more of workers 610. For example, workers 610 may be associated with (e.g., wearing) a motion tracking device (e.g., a step counter, accelerometer, etc.) that generates motion data such that SMS 6 may receive the motion data from the motion tracking device associated with each of workers 610. In some examples, SMS 6 receives data as illustrated in Table 7 below.

TABLE 7

| Worker | Environment | Environment Temp | 15 Min Activity | 30 Min Activity | 15 Min Heart High | 15 Min Heart Low | 15 Min Skin Temp | 15 Min Ear Temp | Humidity |
|---|---|---|---|---|---|---|---|---|---|
| 610A | 602 | 92 | Low | Low | 92 | 82 | 93 | 98 | Low |
| 610B | 602 | 92 | Low | Low | 80 | 78 | 90 | 98 | Low |
| 6106 | 602 | 92 | Low | Low | 127 | 125 | 91 | 101 | Low |
| 610D | 604 | 110 | Low | Low | 150 | 133 | 89 | 98 | Low |
| 610E | 606 | 72 | High | High | 165 | 154 | 85 | 100 | Low |

SMS 6 may determine a safety risk score for each of workers 610. In some examples, SMS 6 determines the respective safety risk scores based at least in part on the physiological data associated with respective worker and a risk profile associated with the respective worker. For example, the risk profile may include historical physiological data for the worker, environmental temperature data, environmental humidity data, and worker activity data (e.g., generated by a step counter). SMS 6 may determine a safety risk score for worker 610D based on the heart rate data, skin temperature data, and ear temperature data for worker 610D, as well as environmental temperature data, environmental humidity data, and worker activity data (e.g., generated by a step counter). In some examples, SMS 6 determines that the safety risk score for worker 610D is "medium" even though the heart rate for worker 610D is between 133 and 150 because the historical physiological data, environmental data, and activity data indicate that worker 610D is well acclimated and able to handle the temperatures with proper ventilation and hydration in addition to a low activity level.

Similarly, SMS 6 may determine that workers 610A and 610B are "low" risk because the physiological data and risk profile indicate that workers 610A and 610B are acclimated to environment 602 and their vital signs are within a normal range for workers 610A, 610B respectively, while working in environment 602. SMS 6 may determine that the safety risk score for worker 610E is "high" because worker 610E has had a high activity level and has a high heart rate as well as high body temperature. For example, the lower skin temperature with the high ear temperature may be an indication of the onset of heat stroke. Thus, SMS 6 may determine that the safety risk score for worker 610E is high.

SMS 6 may determine the safety risk score for worker 610C based on physiological data for worker 610C and physiological data for one or more similar workers. For example, SMS 6 may determine that workers 610A-610C are all similar workers because workers 610A-610C are working in the same environment 602. Thus, SMS 6 may determine the safety risk score for worker 610C based on physiological data for worker 610C and physiological data for workers 610A, 610B. SMS 6 may determine that the safety risk score for worker 610C is "high" because worker 610C has an increased ear temperature relative to workers 610A, 610B and a higher heart rate relative to workers 610A, 610B.

SMS 6 may determine whether any of workers 610A, 610B, 610C, or 610E are replacement workers for worker 610D. In other words, SMS 6 may determine whether to transition any of workers 610A, 610B, 610C, or 610E to environment 604. SMS 6 may determine whether any of workers 610A, 610B, 610C, or 610E are replacements for worker 610D based on the safety risk scores for the respective workers. In some examples, SMS 6 may determine that workers 610C and 610E are not replacements for worker 610D because they have a "high" safety risk score relative to the "medium" safety risk score for worker 610D. However, SMS 6 may determine that either or both of workers 610A, 610B are possible replacements for worker 610E because they have a "low" safety risk score relative to the "medium" safety risk score for worker 610D.

SMS 6 may output a notification indicating the safety risk scores for workers 610. In some examples, the notification indicates whether a respective worker is a possible replacement for another worker, such as worker 610C. In the example, of FIG. 6, the notification may indicate that workers 610A and 610B are possible replacements for worker 610C. In some examples, the notification may indicate whether a particular worker needs additional attention. For example, the notification for worker 610C may indicate that worker 610C is high risk and should be removed from environment 602.

The following numbered examples may illustrate one or more aspects of the disclosure:

Example 1. A method comprising: receiving, by a computing device, from at least one physiological sensor of a personal protective equipment (PPE) device, physiological data indicative of one or more physiological characteristics of a worker; determining, by the computing device, based at least in part on the physiological data and a risk profile associated with the worker, a safety risk score for the worker; and outputting an indication of the safety risk score for the worker.

Example 2. The method of example 1, further comprising: receiving, by the computing device, from a plurality of physiological sensors of a plurality of PPE devices, physiological data indicative of one or more physiological characteristics of a plurality of workers including the worker, wherein the plurality of PPE devices include the PPE device, and wherein the plurality of physiological sensors include the at least one physiological sensor; determining, by the computing device, based at least in part on the physiological data and respective risk profiles for the plurality of workers, respective safety risk scores for the plurality of workers; and outputting by the computing device, an indication of the respective safety risk scores for the plurality of workers.

Example 3. The method of example, further comprising: determining, by the computing device, a relative risk of the worker to other workers of the plurality of workers, wherein the indication of the safety risk score for the worker comprises an indication of the relative risk.

Example 4. The method of any one of examples 1-3, further comprising: determining, by the computing device, based on the risk profile, a worker classification associated with the worker, wherein determining the safety risk score for the worker comprises determining, by the computing device, the safety risk score based at least in part on the physiological data and the worker classification.

Example 5. The method of example 4, wherein determining the worker classification comprises determining the worker classification by at least determining biographical data for the worker, the method further comprising: determining, by the computing device, based on the biographical data of the worker, a group of one or more similar workers, the one or more similar workers represented by biographical data corresponding to the biographical data for the worker; determining, by the computing device, historical physiological data for the group of similar workers; and wherein determining the safety risk score for the worker comprises determining the safety risk score based at least in part on the physiological data for the worker and the historical physiological data for the group of similar workers.

Example 6. The method of any one of examples 1-5, further comprising: determining, by the computing device, a work environment for the worker; determining, by the computing device, based on work environment, a group of one or more similar workers; and determining, by the computing device, physiological data for the group of similar workers; wherein determining the safety risk score for the worker comprises determining the safety risk score for the worker based at least in part on the physiological data for the worker and the physiological data for the group of similar workers.

Example 7. The method of any one of examples 1-6, wherein the risk profile includes a task risk profile indicating a task to be performed by the worker.

Example 8. The method of any one of examples 1-7, wherein the risk profile comprises a user profile including historical physiological data corresponding to the worker.

Example 9. The method of any one of examples 1-8, further comprising: determining, by the computing device, one or more characteristics of a work environment associated with the worker; determining, by the computing device, based on the characteristics of the work environment, historical physiological data corresponding to the worker and to one or more similar work environments; and wherein the safety risk score is based on the physiological data for the worker and the historical physiological data corresponding to the worker and to the one or more similar work environments.

Example 10. The method of any one of examples 1-9, wherein the risk profile comprises sensor data indicative of one or more characteristics of the work environment.

Example 11. The method of any one of examples 1-10, wherein the sensor data indicative of one or more characteristics of the work environment includes at least one of: data indicative of an air quality of the work environment; data indicative of a temperature of the work environment; data indicative of noise in the work environment; or data indicative of radiation in the work environment.

Example 12. The method of example 11, wherein the worker is a first worker and the PPE device is a first PPE device, the method further comprising: receiving, by the computing device, sensor data from a second environmental sensor of a second PPE device associated with a second worker; determining, by the computing device, whether the computing device is receiving sensor data from a first environmental sensor from the first PPE device associated with the first worker; and responsive to determining that the computing device is not receiving sensor data from the first environmental sensor, determining, by the computing device, the safety risk score for the worker further based on the sensor data received from the second environmental sensor.

Example 13. The method of any one of examples 11-12, wherein the at least one physiological sensor includes at least one of: a sweat sensor configured to generate physiological data indicative of perspiration of the worker and configured to measure biomarkers in sweat of the worker, or a temperature sensor configured to measure a core body temperature of the worker.

Example 14. The method of any one of examples 11-13, wherein the worker is a first worker, the method further comprising: determining, by the computing device, based on the safety risk score for the first worker and a safety risk score for a second worker, whether the safety risk score for the second worker is lower than the safety risk score for the first worker; and responsive to determining that the safety risk score for the second worker is lower than the safety risk score for the first worker, outputting, by the computing device, a notification indicating the second worker is a replacement for the first worker.

Example 15. The method of any one of examples 1-14, further comprising: predicting, by the computing device, based at least in part on the safety risk score, whether the worker will experience a safety event; and responsive to predicting that the worker will experience the safety event, outputting, by the computing device, a notification indicating the worker is predicted to experience a safety event.

Example 16. The method of example 15, wherein the safety event includes at least one of: a heat related illness, a cardiac related illness, or a respiratory illness.

Example 17. The method of any one of examples 1-16, wherein the notification indicating the worker is predicted to experience a safety event includes an indication of at least one replacement worker that is not predicted to experience a safety event.

Example 18. The method of any one of examples 1-17, further comprising: predicting, by the computing device, based at least in part on the safety risk score, whether the worker will experience a safety event; and responsive to predicting that the worker will experience the safety event, outputting, by the computing device, to at least one article of personal protective equipment, a command to adjust operation of the at least one article of personal protective equipment.

Although the methods and systems of the present disclosure have been described with reference to specific exemplary embodiments, those of ordinary skill in the art will readily appreciate that changes and modifications may be made thereto without departing from the spirit and scope of the present disclosure.

In the present detailed description of the preferred embodiments, reference is made to the accompanying drawings, which illustrate specific embodiments in which the invention may be practiced.

The illustrated embodiments are not intended to be exhaustive of all embodiments according to the invention. It is to be understood that other embodiments may be utilized and structural or logical changes may be made without departing from the scope of the present invention. The following detailed description, therefore, is not to be taken in a limiting sense, and the scope of the present invention is defined by the appended claims.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

Spatially related terms, including but not limited to, "proximate," "distal," "lower," "upper," "beneath," "below," "above," and "on top," if used herein, are utilized for ease of description to describe spatial relationships of an element(s) to another. Such spatially related terms encompass different orientations of the device in use or operation in addition to the particular orientations depicted in the figures and described herein. For example, if an object depicted in the figures is turned over or flipped over, portions previously described as below or beneath other elements would then be above or on top of those other elements.

As used herein, when an element, component, or layer for example is described as forming a "coincident interface" with, or being "on," "connected to," "coupled with," "stacked on" or "in contact with" another element, component, or layer, it can be directly on, directly connected to, directly coupled with, directly stacked on, in direct contact with, or intervening elements, components or layers may be on, connected, coupled or in contact with the particular element, component, or layer, for example. When an element, component, or layer for example is referred to as being "directly on," "directly connected to," "directly coupled with," or "directly in contact with" another element, there are no intervening elements, components or layers for example. The techniques of this disclosure may be implemented in a wide variety of computer devices, such as servers, laptop computers, desktop computers, notebook computers, tablet computers, hand-held computers, smart phones, and the like. Any components, modules or units have been described to emphasize functional aspects and do not necessarily require realization by different hardware units. The techniques described herein may also be implemented in hardware, software, firmware, or any combination thereof. Any features described as modules, units or components may be implemented together in an integrated logic device or separately as discrete but interoperable logic devices. In some cases, various features may be implemented as an integrated circuit device, such as an integrated circuit chip or chipset. Additionally, although a number of distinct modules have been described throughout this description, many of which perform unique functions, all the functions of all of the modules may be combined into a single module, or even split into further additional modules. The modules described herein are only exemplary and have been described as such for better ease of understanding.

If implemented in software, the techniques may be realized at least in part by a computer-readable medium comprising instructions that, when executed in a processor, performs one or more of the methods described above. The computer-readable medium may comprise a tangible computer-readable storage medium and may form part of a computer program product, which may include packaging materials. The computer-readable storage medium may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The computer-readable storage medium may also comprise a non-volatile storage device, such as a hard-disk, magnetic tape, a compact disk (CD), digital versatile disk (DVD), Blu-ray disk, holographic data storage media, or other non-volatile storage device.

The term "processor," as used herein may refer to any of the foregoing structure or any other structure suitable for implementation of the techniques described herein. In addition, in some aspects, the functionality described herein may be provided within dedicated software modules or hardware modules configured for performing the techniques of this disclosure. Even if implemented in software, the techniques may use hardware such as a processor to execute the software, and a memory to store the software. In any such cases, the computers described herein may define a specific machine that is capable of executing the specific functions described herein. Also, the techniques could be fully implemented in one or more circuits or logic elements, which could also be considered a processor.

What is claimed is:

1. A system comprising:
    a first personal protective equipment (PPE) device configured to be worn by a worker, the first PPE device including a first environmental sensor and at least one breathing sensor configured to generate physiological data indicative of a breathing rate of the worker;
    a second article of PPE device associated with a corresponding worker, the second PPE device including a second environmental sensor; and
    a computing device communicatively coupled to the first PPE device and the second PPE device, the computing device being configured to:
        determine that the computing device is not receiving sensor data from the first environmental sensor;
        responsive to determining that the computing device is not receiving sensor data from the first environmental sensor, identify sensor data received from the second environmental sensor;
        determine, based at least in part on the physiological data, a risk profile associated with the worker, and the sensor data received from the second environmental sensor, a safety risk score for the worker, the safety risk score being associated with a likelihood of whether the worker will experience a respiratory illness related safety event;
        output an indication of the safety risk score for the worker;
        determine that the safety risk score satisfies a threshold safety risk score;
        based on the determination that the safety risk score satisfies the threshold safety risk score, to an emergency response unit, an alert comprising an indication of at least one replacement worker who is not predicted to experience the respiratory illness related safety event;
        responsive to determining that the safety risk score satisfies the threshold safety risk score, output to the first PPE device a command to adjust an operation of the first PPE device at least in part by increasing an oxygen flow rate of the first PPE device.

2. The system of claim 1, further comprising a plurality of PPE devices that include the first PPE device and the second PPE device, wherein the plurality of PPE devices each include at least one breathing sensor of a plurality of breathing sensors, wherein the plurality of breathing sensors include the at least one breathing sensor, wherein the plurality of breathing sensors are configured to generate respective sets of physiological data indicative of respective breathing rates of a plurality of workers including the worker, wherein the computing device is further configured to:

determine, based at least in part on the physiological data and respective risk profiles for the plurality of workers, respective safety risk scores for the plurality of workers; and output respective indications of the respective safety risk scores for the plurality of workers.

3. The system of claim 2, wherein the computing device is further configured to determine a relative risk of the worker with respect to one or more other workers of the plurality of workers, and wherein the indication of the safety risk score for the worker comprises an indication of the relative risk.

4. The system of claim 1, wherein the computing device is further configured to determine, based on the risk profile, a worker classification associated with the worker, wherein to determine the safety risk score for the worker, the computing device is configured to determine the safety risk score based at least in part on the physiological data and the worker classification, wherein the risk profile indicates a classification of the worker, and wherein to determine the safety risk score for the worker, the computing device is configured to determine the safety risk score based at least in part on the classification of the worker.

5. The system of claim 4, wherein the computing device is configured to determine the worker classification at least in part by determining biographical information for the worker, and wherein the computing device is further configured to:

determine, based on the biographical information of the worker, a group of one or more similar workers with respect to the worker, the one or more similar workers represented by biographical information corresponding to the biographical information for the worker; and determine historical physiological information for the group of similar workers, wherein to determine the safety risk score for the worker, the computing device is configured to determine the safety risk score based at least in part on the physiological data for the worker and the historical physiological information for the group of similar workers.

6. The system of claim 1, wherein the computing device is further configured to:

determine a work environment for the worker;

determine, based on the work environment determined for the worker, a group of one or more similar workers with respect to the worker; and determine respective physiological data for each respective similar worker of the group of similar workers, wherein to determine the safety risk score for the worker, the computing device is configured to determine the safety risk score based at least in part on the physiological data for the worker and the respective physiological data for each respective similar worker of the group of similar workers.

7. The system of claim 1, wherein the risk profile includes a task risk profile indicating a task to be performed by the worker, and wherein to determine the safety risk score for the worker, the computing device is configured to determine the safety risk score for the worker based on the task risk profile.

8. The system of claim 1, wherein the risk profile comprises a user profile including historical physiological data corresponding to the worker.

9. The system of claim 8, wherein the computing device is further configured to:

determine one or more characteristics of a work environment associated with the worker; and determine, based on the characteristics of the work environment, historical physiological data that corresponds to the worker and to one or more similar work environments with respect to the work environment, wherein to determine the safety risk score, the computing device is configured to determine the safety risk score based on the physiological data for the worker and the historical physiological data that corresponds to the worker and to the one or more similar work environments.

10. The system of claim 9, wherein the risk profile comprises sensor data indicative of one or more characteristics of the work environment.

11. The system of claim 10, wherein the sensor data indicative of one or more characteristics of the work environment includes at least one of:

data indicative of an air quality of the work environment, data indicative of a temperature of the work environment, data indicative of noise in the work environment, or data indicative of radiation in the work environment.

12. The system of claim 1, wherein the worker is a first worker, and wherein the computing device is further configured to:

determine, based on the safety risk score for the first worker and a safety risk score for a second worker, whether the safety risk score for the second worker is lower than the safety risk score for the first worker; and responsive to determining that the safety risk score for the second worker is lower than the safety risk score for the first worker, output a notification indicating that the second worker is a replacement for the first worker.

13. A computing device comprising:

at least one processor;

memory in communication with the at least one processor, the memory comprising instructions that, when executed, cause the at least one processor to:

receive, from a first personal protective equipment (PPE) device, physiological data indicative of a breathing rate of a worker;

determine, based at least in part on the physiological data and a risk profile associated with the worker, a safety risk score for the worker;

determine that the computing device is not receiving sensor data from the first environmental sensor;

responsive to determining that the computing device is not receiving sensor data from the first environmental sensor, identify sensor data received from a second PPE device, form an indicator of the safety risk score for the worker;

determine that the safety risk score satisfies a threshold safety risk score;

based on the determination that the safety risk score satisfies the threshold safety risk score, form an alert comprising an indication of at least one replacement worker who is not predicted to experience the respiratory illness related safety event;

responsive to determining that the safety risk score satisfies the threshold safety risk score, form a command to adjust an operation of the first PPE device at least in part by increasing an oxygen flow rate of the first PPE device; and interface hardware configured to:
output, to the first PPE device, an indication of the safety risk score for the worker; and
determine that the safety risk score satisfies a threshold safety risk score;
output the alert to an emergency response unit; and
output the command to the first PPE device.

14. The computing device of claim 13, wherein the memory further comprises instructions, that, when executed, cause the at least one processor to:
receive, from a plurality of PPE devices that include the first PPE device and the second PPE device, physiological data indicative of respective breathing rates of a plurality of workers including the worker;
determine, based at least in part on the physiological data and respective risk profiles for the plurality of workers, respective safety risk scores for each respective worker of the plurality of workers; and
output, via the interface hardware, respective indications of the respective safety risk scores for each of the plurality of workers.

15. The system of claim 9, wherein to determine the safety risk score, the computing device is configured to determine that the breathing rate of the worker is outside of a normal breathing rate associated with the worker based on the historical physiological data that corresponds to the worker and to the one or more similar work environments.

16. The system of claim 5, wherein to determine the safety risk score, the computing device is configured to determine that the breathing rate of the worker is outside of a normal breathing rate associated with the worker based on the historical physiological data for the group of similar workers.

* * * * *